US011291505B2

(12) United States Patent
Ahmad

(10) Patent No.: US 11,291,505 B2
(45) Date of Patent: Apr. 5, 2022

(54) SYSTEM FOR SIMULATION FOR THE DEVELOPMENT AND OPTIMIZATION OF PERSON SPECIFIC SURGICAL METHODS AND MATERIALS: THORAX SIMULATION APPARATUS, SYSTEM AND PROCESS

(71) Applicant: Deakin University, Geelong (AU)

(72) Inventor: Rashid Ahmad, Highton (AU)

(73) Assignee: Deakin University, Geelong (AU)

( * ) Notice: Subject to any disclaimer, the term of this patent is extended or adjusted under 35 U.S.C. 154(b) by 546 days.

(21) Appl. No.: 16/071,470

(22) PCT Filed: Jan. 19, 2017

(86) PCT No.: PCT/AU2017/050035
§ 371 (c)(1),
(2) Date: Jul. 19, 2018

(87) PCT Pub. No.: WO2017/124145
PCT Pub. Date: Jul. 27, 2017

(65) Prior Publication Data
US 2019/0015161 A1 Jan. 17, 2019

(30) Foreign Application Priority Data
Jan. 21, 2016 (AU) ................ 2016900189

(51) Int. Cl.
*A61B 34/10* (2016.01)
*A61B 5/00* (2006.01)
(Continued)

(52) U.S. Cl.
CPC .......... *A61B 34/10* (2016.02); *A61B 5/0053* (2013.01); *A61B 5/055* (2013.01); *A61B 5/4538* (2013.01);
(Continued)

(58) Field of Classification Search
CPC ...... A61B 2034/105; A61B 2560/0223; A61B 2576/02; A61B 34/10; A61B 5/0053; A61B 5/055; A61B 5/08; A61B 5/4538; A61B 5/6823; A61F 5/37; G06T 7/0012; G09B 23/30; G16H 30/40; G16H 40/40; G16H 40/60; G16H 50/50
See application file for complete search history.

(56) References Cited

U.S. PATENT DOCUMENTS

| | | | |
|---|---|---|---|
| 2005/0256686 A1* | 11/2005 | Stabelfeldt | G06F 30/23 703/6 |
| 2006/0278245 A1* | 12/2006 | Gan | A61B 5/12 128/898 |

(Continued)

OTHER PUBLICATIONS

International Search Report dated Apr. 18, 2017 for PCT Application No. PCT/AU2017/050035 filed Jan. 19, 2017.
(Continued)

*Primary Examiner* — Pascal M Bui Pho
*Assistant Examiner* — Alexei Bykhovski
(74) *Attorney, Agent, or Firm* — Knobbe, Martens, Olson & Bear, LLP

(57) ABSTRACT

A system for simulating surgical methods includes a method for thorax simulation modelling. The thorax simulation modeling is generally useful in facilitating the development and optimization of person specific surgical methods and materials.

8 Claims, 23 Drawing Sheets

(51) Int. Cl.

| | |
|---|---|
| *A61B 5/055* | (2006.01) |
| *G06T 7/00* | (2017.01) |
| *G09B 23/30* | (2006.01) |
| *A61F 5/37* | (2006.01) |
| *G16H 50/50* | (2018.01) |
| *G16H 40/60* | (2018.01) |
| *G16H 40/40* | (2018.01) |
| *G16H 30/40* | (2018.01) |
| *A61B 5/08* | (2006.01) |

(52) U.S. Cl.
CPC .............. *A61B 5/6823* (2013.01); *A61F 5/37* (2013.01); *G06T 7/0012* (2013.01); *G09B 23/30* (2013.01); *G16H 30/40* (2018.01); *G16H 40/40* (2018.01); *G16H 40/60* (2018.01); *G16H 50/50* (2018.01); *A61B 5/08* (2013.01); *A61B 2034/105* (2016.02); *A61B 2560/0223* (2013.01); *A61B 2576/02* (2013.01)

(56) References Cited

U.S. PATENT DOCUMENTS

2008/0033442 A1* 2/2008 Amiot .................. A61B 5/1077
606/80

2014/0270446 A1 9/2014 Vija
2016/0140758 A1* 5/2016 Ooga .................... A61B 5/0033
382/128

OTHER PUBLICATIONS

Au, O. et al., "Skeleton extraction by mesh contraction." ACM Transactions on Graphics (TOG). 2008, vol. 27, No. 3, Article 4, pp. 44:1-44:10.

Jacobo, A.M., 'Influence of Age Specific Parameters on the Thoracic Response under Controlled belt Loading Conditions', International Journal of Automotive Engineering. 2015, vol. 6, pp. 83-90.

Pazokifard, B. et al., '3-D Segmentation of Human Sternum in Lung MDCT Images,' IEEE Engineering in Medicine and Biology Society, 35th Annual International Conference. Osaka: IEEE 2013, pp. 3351-3354.

Zhao, Q. et al., 'Cartilage Estimation in Noncontrast Thoracic CT,' IEEE 11th International Symposium on Biomedical Imaging. IEEE, 2014, pp. 409-412.

Zhao, Q. et al., 'Chest Modeling and Personalized Surgical Planning for Pectus Excavatum,' International Conference on Medical Image Computing and Computer-Assisted Intervention, Springer International Publishing: 2014, pp. 512-519.

* cited by examiner

SYSTEM FOR SIMULATION FOR THE DEVELOPMENT AND OPTIMIZATION OF PERSON SPECIFIC SURGICAL METHODS AND MATERIALS: THORAX SIMULATION APPARATUS, SYSTEM AND PROCESS

PRIORITY AND CROSS REFERENCE TO RELATED APPLICATIONS

This application is the U.S. National Phase Application under 35 U.S.C. § 371 of International Application No. PCT/AU2017/050035, filed Jan. 19, 2017, designating the U.S. and published in English as WO 2017/124145 A1 on Jul. 27, 2017, which claims the benefit of Australian Patent Application No. AU 2016900189, filed Jan. 21, 2016. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present invention relates to apparatuses, systems and processes for in vivo and person specific simulation, e.g., of the human thorax, e.g., for development and optimization of person specific surgical methods and materials.

BACKGROUND

Simulation technology in mechanical engineering during product development is used routinely with the benefits of reduced development time, prototypes and development cost. Prior applications of this simulation technology to the human body are either limited to component analysis or to crash and/or accident simulation. Component analysis addresses only local limbs' behaviour in isolation, which cannot be applied for total body behaviour in interaction with other body parts. Crash and accident simulation is mainly for dynamic energy dissipation. To accurately simulate the human thorax for applications such as the development and optimization of person specific surgical methods and materials, in vivo and person specific detailed complex non-linear static simulation is required.

It is desired to address or ameliorate one or more limitations or disadvantages in prior art systems and method, or to at least provide a useful alternative.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

SUMMARY

In accordance with the present invention there is provided a process for thorax simulation modelling, including:
  receiving imaging data representing one or more images of a thorax of an individual;
  processing the imaging data to generate component data representing thoracic body parts including one or more joints adjacent to a costal cartilage or a sternum of the individual; and
  processing the generated component data to generate simulation model data representing the structural properties of the thorax of the individual, including the properties of the one or more joints.

The present invention also provides a process for thorax modelling under a compressive load, including:
  determining one or more compressive load levels to be applied to a thorax of an individual;
  applying one or more of the determined compressive loads to the thorax of the individual;
  generating, for each of said applied compressive load levels, imaging data representing one or more images of the thorax region of the individual, when the said compressive load level is applied to the thorax of the individual;
  processing the imaging data to generate component data representing thoracic body parts including one or more joints adjacent to a costal cartilage or a sternum of the individual; and
  processing the generated component data to generate simulation model data representing the structural properties of the thorax of the individual, including the properties of the one or more joints.

The present invention also provides an apparatus for applying compressive loads to a human thorax of an individual during medical imaging, including:
  a compression plate, with first and second flat surfaces, and with one or more attachments;
  strapping, at least partially bound to the compression plate via the one or more attachments; and
  one or more compression calibration devices attached to the strapping.

The present invention also provides a method of using the apparatus.

BRIEF DESCRIPTION OF THE DRAWINGS

Some embodiments of the present invention are hereinafter described, by way of example only, with reference to the accompanying drawings, in which.

DETAILED DESCRIPTION

Overview

Described herein are an apparatus, a system and a process for thorax simulation and "modelling".

The system and process use medical images of a thorax of a specific person to simulate structural behaviour of the thorax of that person. The simulation is three-dimensional, and models structural properties of the thorax sub-parts, including the ribs, sternum and costal cartilage, of the specific person. The simulation is non-linear and static.

The simulation modelling system and process utilise medical imaging data, which are processed to generate component data representing the thorax sub-parts of the individual person. The medical images capture the thorax sub-parts' structures—the ribs, the sternum, and the costal cartilage including soft tissues (muscles)—and are taken while the individual is alive such that the modelling is 'in-vivo'.

Each sub-part is represented in the form of a Computer Aided Design (CAD) model, and the CAD models are collectively processed to generate a simulation model which captures the structural properties of joints adjacent to the costal cartilage or sternum. In one embodiment of the described system and process, imaging data is generated by performing medical scanning of the individual's thorax region. In alternative embodiments, the simulation modelling is performed using medical image data received by the system from an external source, such as, for example, medical images produced during previous scans of the individual's thorax region.

The apparatus for thorax modelling is configured to apply a compressive load (or "force") to the thorax of the individual via a compression plate. The apparatus includes strapping that is configured to cause the compression plate to apply the constant compressive load at a selected one of a plurality of predetermined levels. Medical images are generated of the individual's thorax while the compressive load is applied at one of the predetermined levels. These medical images are processed to generate the component data for the thorax sub-parts of the individual person for each applied load level.

The resulting simulation model of the individual's thorax can be used to simulate interactions of surgical methods and surgical tools with the individual's thorax before any surgery takes place. This can allow selection and adaption of the surgical methods and the surgical tools for the unique anatomical characteristics of the individual with improved efficiency and safety.

Description of the System

Figure 1A:
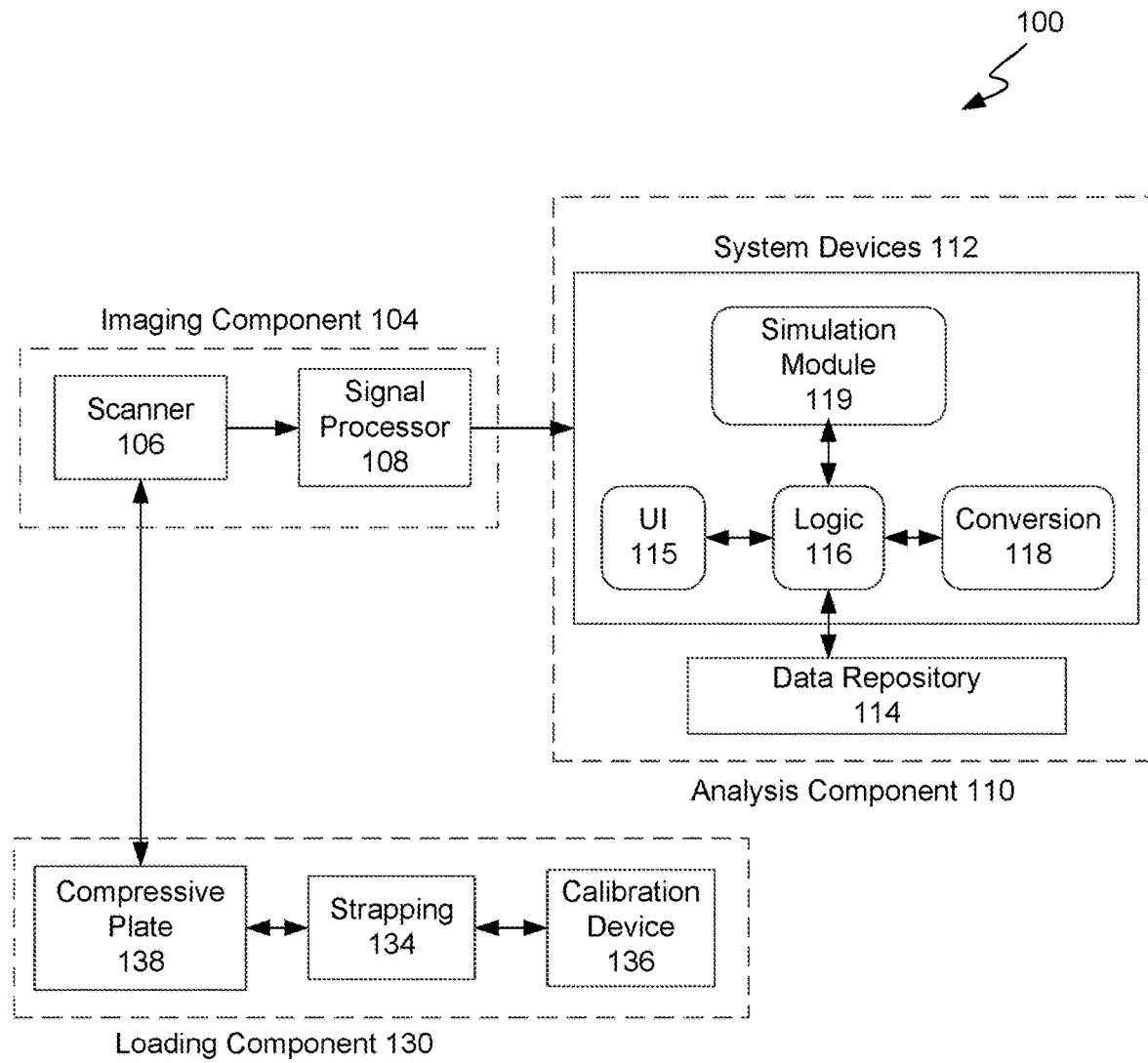
FIG. 1a is a schematic diagram of a system for thorax simulation.

As shown in FIG. 1a, a simulation modelling system 100 includes an imaging component 104, an analysis component 110 and a loading component 130. The imaging component 104 includes a scanner 106 and a signal processor 108. The scanner 106 can be a Magnetic Resonance Imaging (MRI) scanner, and the diagnostic signals can include magnetic fields and radio wave signals.

The signal processor 108 is in electronic communication with the scanner 106. The signal processor 108 receives medical imaging signals from the scanner 106, and generates imaging data, from the imaging signals, representing the in-vivo medical images of an individual.

The analysis component 110 includes system devices 112 that include one or more computing devices, such as data and/or application servers, or computational workstations, which are configured to process the medical imaging data of the individual. The system devices 112 include software modules that control the analysis component 110, including:

(i) a user interface (UI) module 115;
(ii) a logic module 116;
(iii) a conversion module 118; and
(iv) a simulation module 119.

The system devices 112 include one or more microprocessors that read and execute machine-readable code representing the software modules to control the analysis component. The system devices 112 include a visible display for displaying data from the UI 115, and one or more human input devices (e.g., keyboards, mice, touchscreens, haptic devices) for and receiving human input for the UI 115.

The analysis component 110 includes a data repository 114 configured to receive, store and send data representing the medical images, the thorax sub-parts, the simulation models, and validation results for each individual. The data repository 114 can be referred to as "data storage". The data repository 114 includes a file management system (FMS) and/or a database management system (BDMS) for storage and retrieval of data in the data repository 114. The medical images of each individual can be stored and retrieved at a later time for simulation and validation when appropriate. The repository 114 can be configured to store anatomical models of the thorax sub-parts to allow simulation with data previously generated.

Figure 1B:
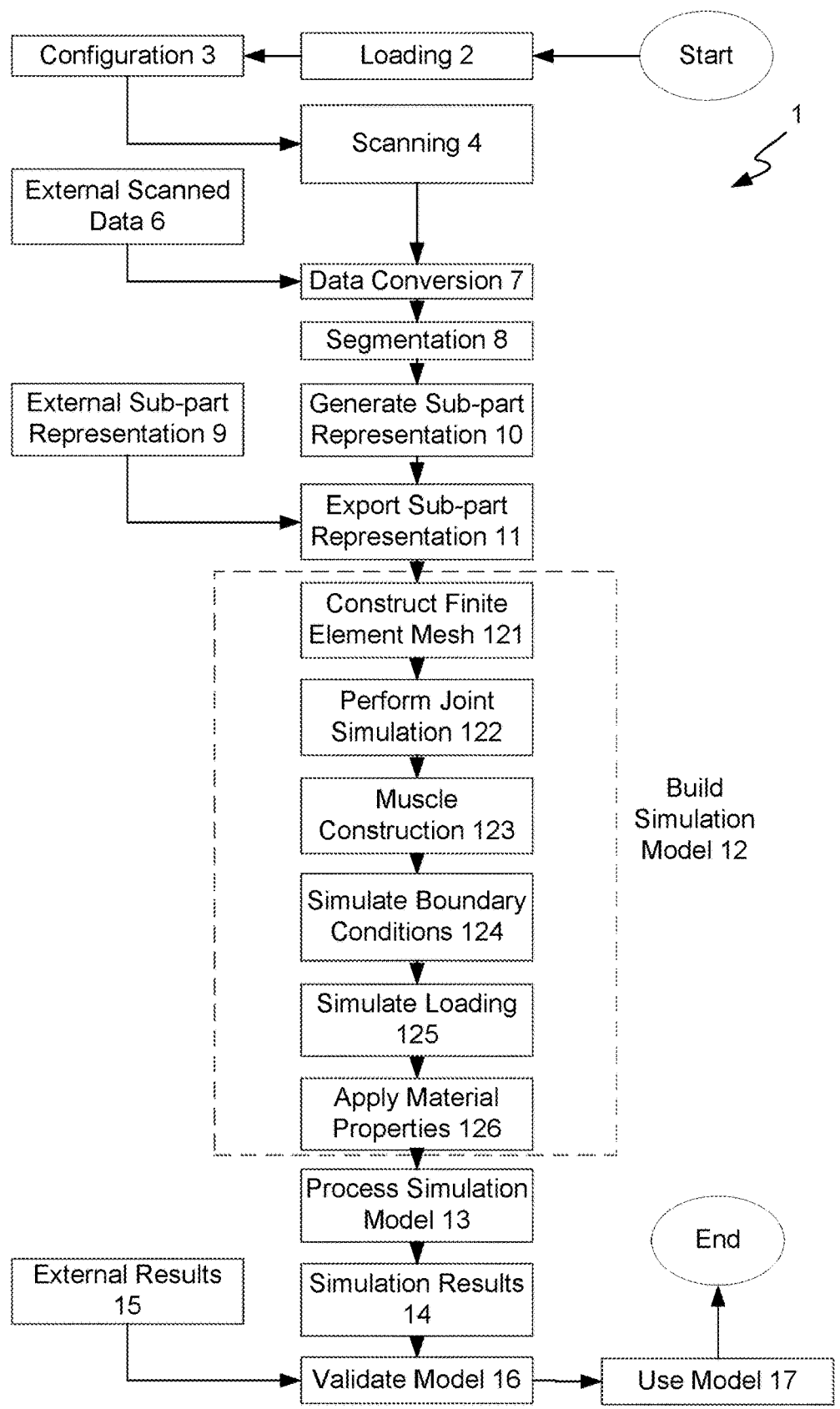
FIG. 1b is a flow diagram of a simulation process performed by the system.

The system 100 is configured to perform a simulation model generation process 1 (also referred to as a "simulation model construction process"). In the simulation model generation process 1, the individual is positioned on a bed or table (such as an MRI table) for the acquisition of medical imaging data if required. As shown in FIG. 1b, the individual's thorax is loaded (step 2) using a compression apparatus, the scanner is configured (step 3), and scanning (step 4) is performed under no load and under various safe load conditions as necessary. Data is produced for each scanning session. Scanned data is converted (step 7) into a format readable for the segmentation process (step 8). Alternatively, or in addition, scanned data obtained from external sources can be used in the same manner as newly produced data (step 6). The scanned medical imaging data is imported into the segmentation software and an entry in the database is created. Using this database entry, the individual body parts (including the thorax sub-parts) are obtained and stored. The individual body parts are exported from the segmentation software into a CAD-system part by part. The individual body parts are converted into CAD-solids if required using CAD-system options available in the CAD-system. These individual body parts are then represented as CAD-parts in the CAD-system, and the assemblies required to generate the sub-part representations are created (step 10). All these CAD-parts and assemblies correspond to the scanned living individual, and as such are "in-vivo person specific" sub-part models. CAD-parts from external sources can be added alternatively or in addition to the generated sub-parts (step 9).

The simulation model generation process 1 involves several sub processes. The CAD-parts are exported from the CAD-system 11 into a third party finite element software system (step 11) and a mesh (represented by mesh data) is created in the finite element software system using exported CAD-parts (step 121). The mesh data are supplemented with additional data produced from the joint simulation (step 122), skin construction (step 123), boundary condition simulation (step 124), loading simulation (step 125), and material property application processes (step 126). A simulation model is built in the finite element software system using the data created by the processes in steps 122, 123, 124, 125 and 126. The simulation model is processed (step 13), and the results 14 are obtained and correlated to the external results 15 from other sources (obtained in step 15). Once the results are correlated and the model is validated in step 16, the simulation model and results can be used for applications (step 17), such as the development and optimization of person specific surgical methods and materials.

The sections hereinafter describe the system and process shown in FIGS. 1*a* and 1*b*, in the context of thorax simulation modelling as performed on a scenario involving an individual, e.g., a volunteer representing a 50th percentile adult male.

1. Compressive Loading of the Thorax

As shown in FIG. 1*b*, simulation modelling involves the application of compressive loads to the individual's thorax. A person specific maximum load value must be determined and approved by the relevant medical specialist (cardiothoracic surgeon). The location of load application on human body, nature and method of load application must also be approved by the relevant medical specialist (cardiothoracic surgeon). The loading system explained in this section is used to validate the simulation modelling system and process described herein.

1.1 Loading the Individual

As the medical imaging and simulation is performed in-vivo, the loading method must:
  i) be safe for the individual;
  ii) give reasonable deflection to avoid any numerical noise;
  iii) be capable of being accommodated in an MRI-gantry;
  iv) be capable of applying loads that are accurately measurable; and,
  v) in case of emergency, be capable of being immediately removed from the individual.

Loading is achieved by a loading component 130, as shown in FIG. 1*a*, that is configured to apply controlled compressive loads to the thorax, while the individual is positioned within the scanner 106. The loading component 130 includes a compression plate 138 (also referred to as a "compressive plate" or a "loading plate"), a strapping 134 and a calibration device 136. The loading component 130 applies a vertical load (or "force") to the chest of the individual through the compression plate 138 mounted on the individual's chest.

1.2 Size and Placement of the Compression Plate

Design of the compression plate 138 is influenced by:
  (i) the structural mechanics involved in the thorax area;
  (ii) the anatomical structure of the thorax; and
  (iii) the position of the internal organs.

The compression plate 138 has dimensions sufficient to cover at least the portion of the individual's thoracic region as required to accurately image the thorax sub-parts under compression, where the bottom plate surface is positioned on the thorax of the individual and is oriented parallel with the surface of the individual's chest.

Figure 2:
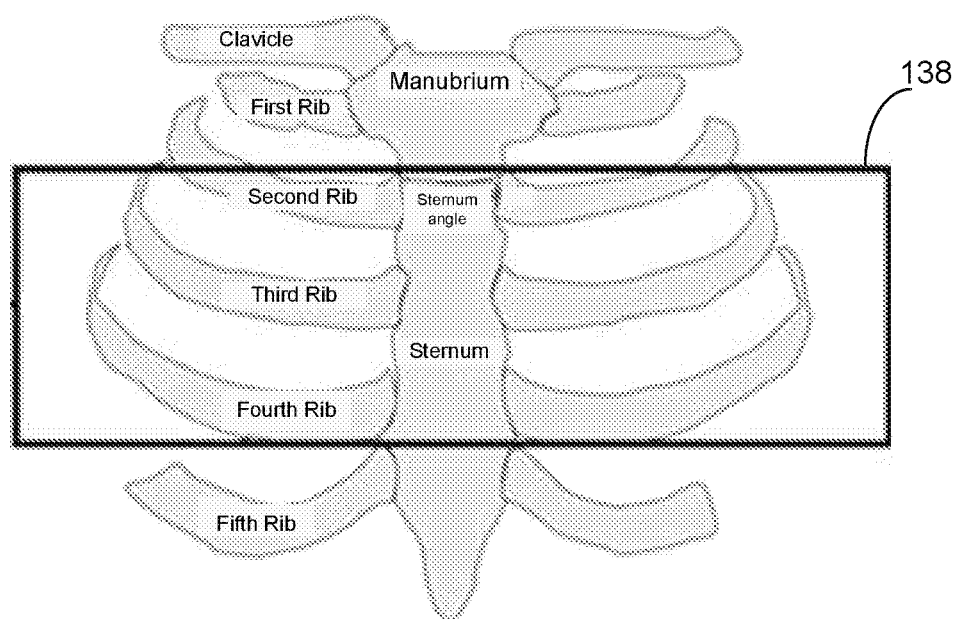
FIG. 2 is a diagram showing positioning of a compression plate during operation of the system.

The compression plate 138 is positioned such that its upper edge is about 5 mm above the manubrium edge of the manubriosternal joint/sternum angle. The lower edge of the plate just covers the fourth costal cartilage and does not cover any portion of the fifth costal cartilage, as shown in FIG. 2. This is to avoid any direct loading to the fifth costal cartilage which can cause injuries to the individual.

1.3 Material of the Compression Plate

The material of the compression plate 138 is chosen such as to fulfil the following requirements:
  i. possess sufficient rigidity and strength to transfer the load to the individuals chest without sustaining any local deformation or without requiring unreasonable thickness such that it is prevented from being accommodated in the MRI-gantry;
  ii. non-ferrous to be safe in an MRI-gantry; and
  iii. allows accurate medical scanning of the human body underneath the plate during scanning.

As a result, the plate 138 can be formed of non-conducive and non-magnetic material, including a piece of dry hard wood that is flat and rectangular in shape, as used in the system described herein.

1.4 Loading Mechanism

The strapping 134 is configured to secure the compression plate 138 against the individual's thorax region, and to exert the compressive load onto the thorax. The compression plate 138 includes attachment pieces at its opposing sides to attach the strapping 134 the compression plate 138. The strapping 134 is configured to be attached to the scanning bed, bench, or table on which the individual is positioned during the scanning. The plate 138 and strapping 134 may be configured for use with a horizontally aligned table, and/or when medical scanning is performed with the individual in a standing position braced against a vertical supporting structure.

Figure 3:
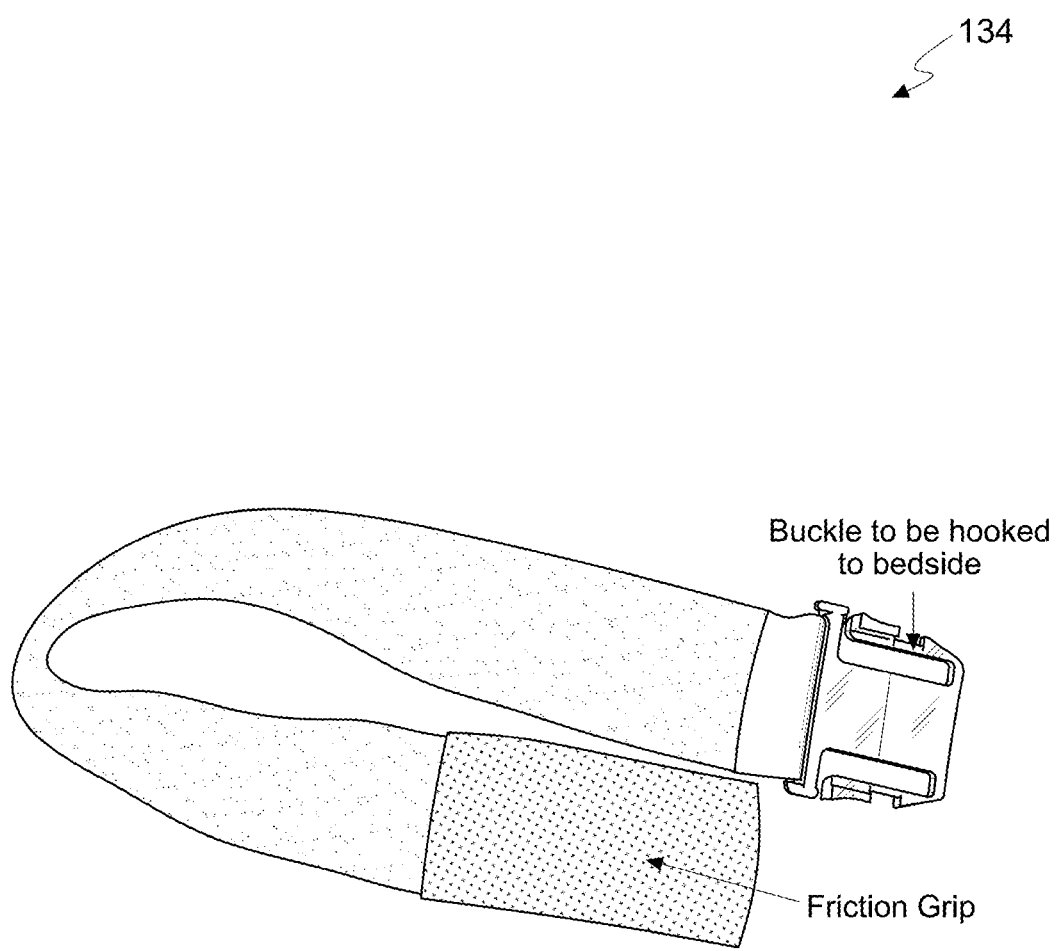
FIG. 3 is a photograph of a portion of friction grip and strapping of a compressive loading apparatus.
Figure 4:
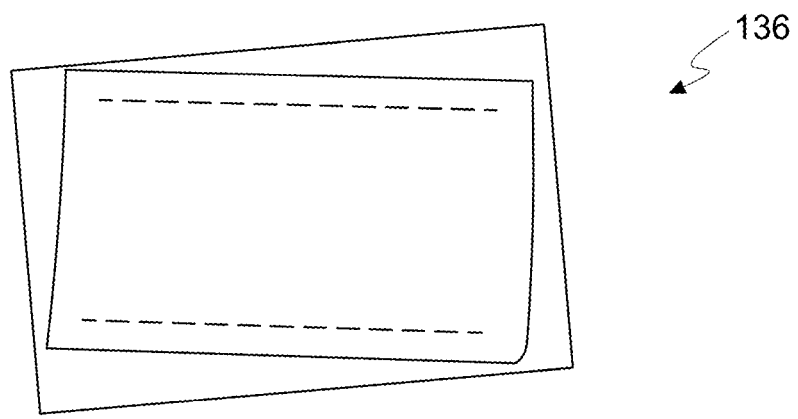
FIG. 4 is a photograph of an attachment piece of the compressive loading apparatus.
Figure 5:
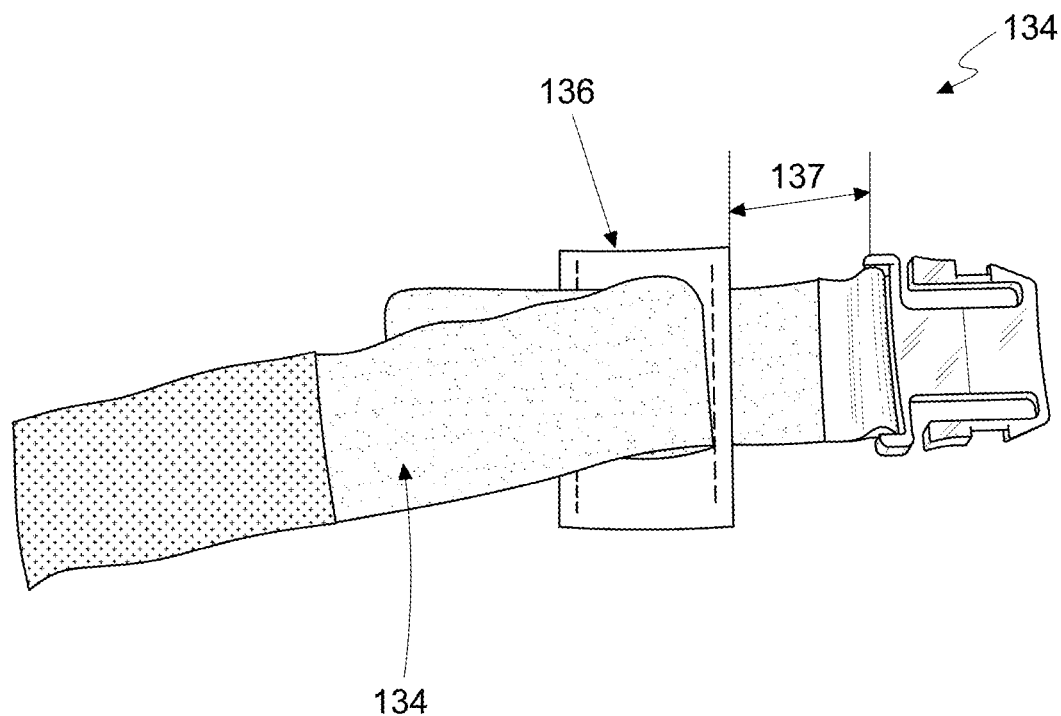
FIG. 5 is a photograph of the strapping and attachment piece.
Figure 6:
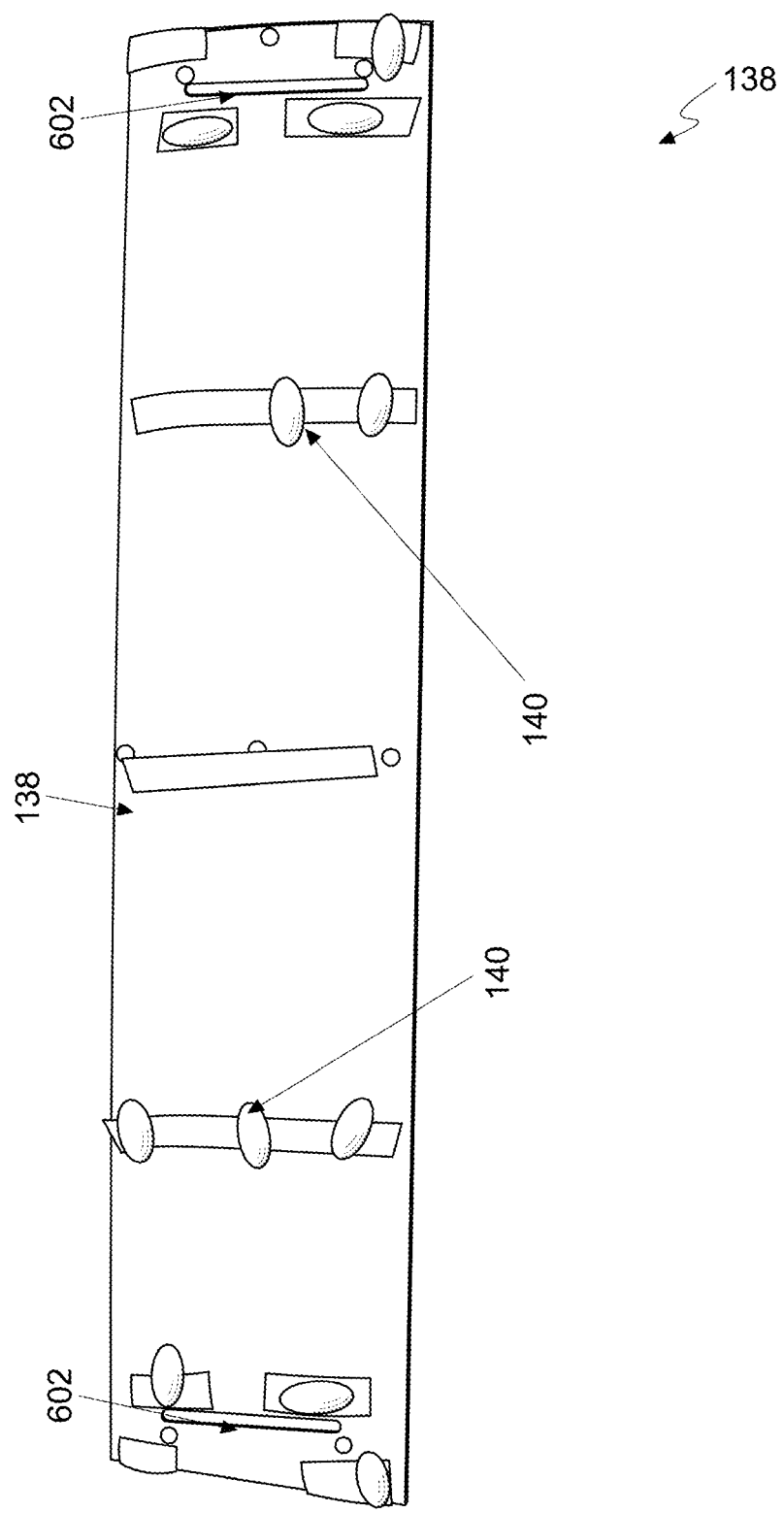
FIG. 6 is a photograph of the compression plate of a compressive loading apparatus.
Figure 7:
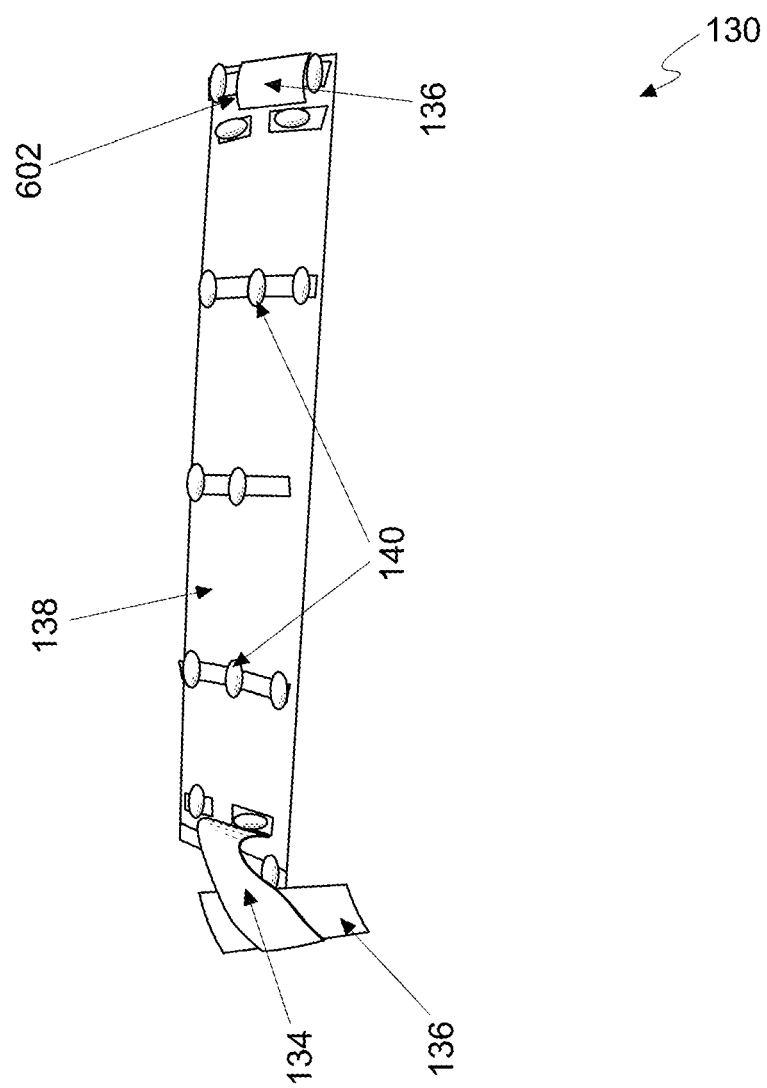
FIG. 7 is a photograph of the compression plate and attached strapping of the compressive loading apparatus.

In the described system, the strapping 134 is in the form of the existing straps of the MRI table on which the individual is positioned during scanning. These MRI-straps are normally used to hold the magnetic coils in position. They cannot be used as such to pull the plate downwards to apply load to the individual's chest because even in their fully pulled position when buckled to the MRI-couch side, there is negligible tension in the straps and hence negligible pressure on the chest. The friction grip on the straps can be modified using a rectangular piece of hook-and-loop tape (e.g., "Velcro") as explained in FIG. 3 to FIG. 5. Slots 602 are made in the loading plate 138 to pass though the straps as depicted in FIG. 6 and FIG. 7. The plate 138 is mounted on the individual's chest, straps are passed through the slots 602 on each side, pulled down and the strap ends buckled to the MRI-couch side.

1.5 Dimensioning and Making the Loading Plate

The dimensions of the finished loading plate 138 is exact within 1.5 mm tolerances. When mounted to the individual's chest, positioned and loaded must fulfil the specifications explained in section 1.2.

Due to MRI-gantry environments, it is almost impossible to carry out the dimension analysis in the MRI-gantry with the individual positioned in it to dimension the loading plate. Therefore, the following procedure is adopted for dimensioning the plate:

i. a cardboard prototype of the loading plate with approximate dimension is made;

ii. the individual is positioned in the MRI-gantry, and the cardboard prototype is mounted on his/her chest, and scanning of the thorax is carried out;

iii. based upon the scan information step ii., the dimensions of the cardboard prototype are modified to fulfil the requirements under section 1.2;

iv. the cardboard prototype dimensions are used to produce a 12 mm thick softwood prototype;

v. the softwood prototype is mounted on the individual's chest and slightly loaded in the presence of a thoracic surgeon, enabling thorax scanning to be carried out under these conditions;

vi. based upon the scan information under step v, the soft wood prototype is modified to fulfil the requirements under section 1.2;

vii. step v and vi are repeated until the prototype of soft wood loading plate is within 1.5 mm tolerances; and viii. the final softwood prototype from step vii is copied using a numerically controlled (NC) an NC-machine to produce a 12 mm thick hard wood loading plate, with the slots 602 at both ends to pass through the loading straps.

The edges of the loading plate 138 are rounded to avoid injuries to the chest. The dimensions of the compression plate 138 used in the described embodiments are 500 by 100 by 12 mm, as was determined to be suitable for the 50th percentile adult male volunteer based on the procedure described hereinbefore.

The compression plate 138 also includes one or more guide elements attached to the top and/or bottom surfaces. The guide elements are distinguishable from the remainder of the plate 138 within medical imaging data generated using the plate 138 (as described hereinafter). This allows for the visual identification of the position of the plate 138 on the individual's thorax within the images of the individual's compressed thorax.

1.6 Determination of the Maximum Safe Load for the Individual

The maximum safe load is determined for the individual by a relevant medical specialist, such as a thoracic surgeon, according to the following process. The individual lies on his back on a patient bed similar to MRI-gantry couch, the hardwood loading plate is positioned by the surgeon on his chest according to the specifications in section 1.2. Incremental weights are put on the hardwood plate. Each time by load increase, the surgeon monitors the effect of the loading upon the individual's wellbeing. In one example, a maximum safe load of 100 N was determined and approved by the surgeon for an individual.

1.7 Calibration of Loading Mechanism

The loading component 130 includes a calibration device 136. For load application, the compression plate 138 includes attachment slots 602, and the strapping 134 passes through the attachment slots 602 to attach the compression plate 138 to the scanning apparatus 106.

The calibration device 136 allows thorax imaging to be performed in the presence of a constant applied compressive force of arbitrary magnitude. The calibration device 136 can include a strip of hook-and-loop fabric (e.g., Velcro) and a fastening mechanism (e.g., a clip) to hold the tightened strapping 134, such that a load within a given range is applied to the thorax of the individual. The calibration device 136 can be a rectangular piece made from Velcro to hold the strap together in the loading position. Tightening of the strapping 134 results in the extension of a calibration length of the calibration device 136, and the calibration length is configured according to a process described hereinafter in Section 1.7.1.

1.7.1 Determination of the Calibration Length

The individual is positioned in the MRI-gantry, the loading plate is mounted using straps, the straps are pulled and the Velcro piece mentioned under section 1.4, is positioned so that there is no looseness and tightness in the strap and the plate is held in its position. The calibration length 137 is then the length of the strap between the edge of the Velcro piece and the centre line of the buckle where the other end of the strap is sewed to (see FIG. 5 in section 1.4), e.g., 38.1 mm. The position of the Velcro piece on the strap is configured such that during pulling the strap for applying load to the individual, the Velcro piece position remains reasonably close to the hinge under full safe load, about 50 N on each side, and does not touch the individual's body. Moreover, the strapping 134 along the calibration length 137 remains of a single thickness during application of the load to the individual, and this is achieved by pulling the strapping 134 and holding it in a pulled position through a Velcro friction grip during the scanning procedure for the maximum safe load case. These requirements lead to 38.1 mm calibration length 137, as shown in FIG. 5.

1.7.2 Calibrating the calibration length

Figure 8:
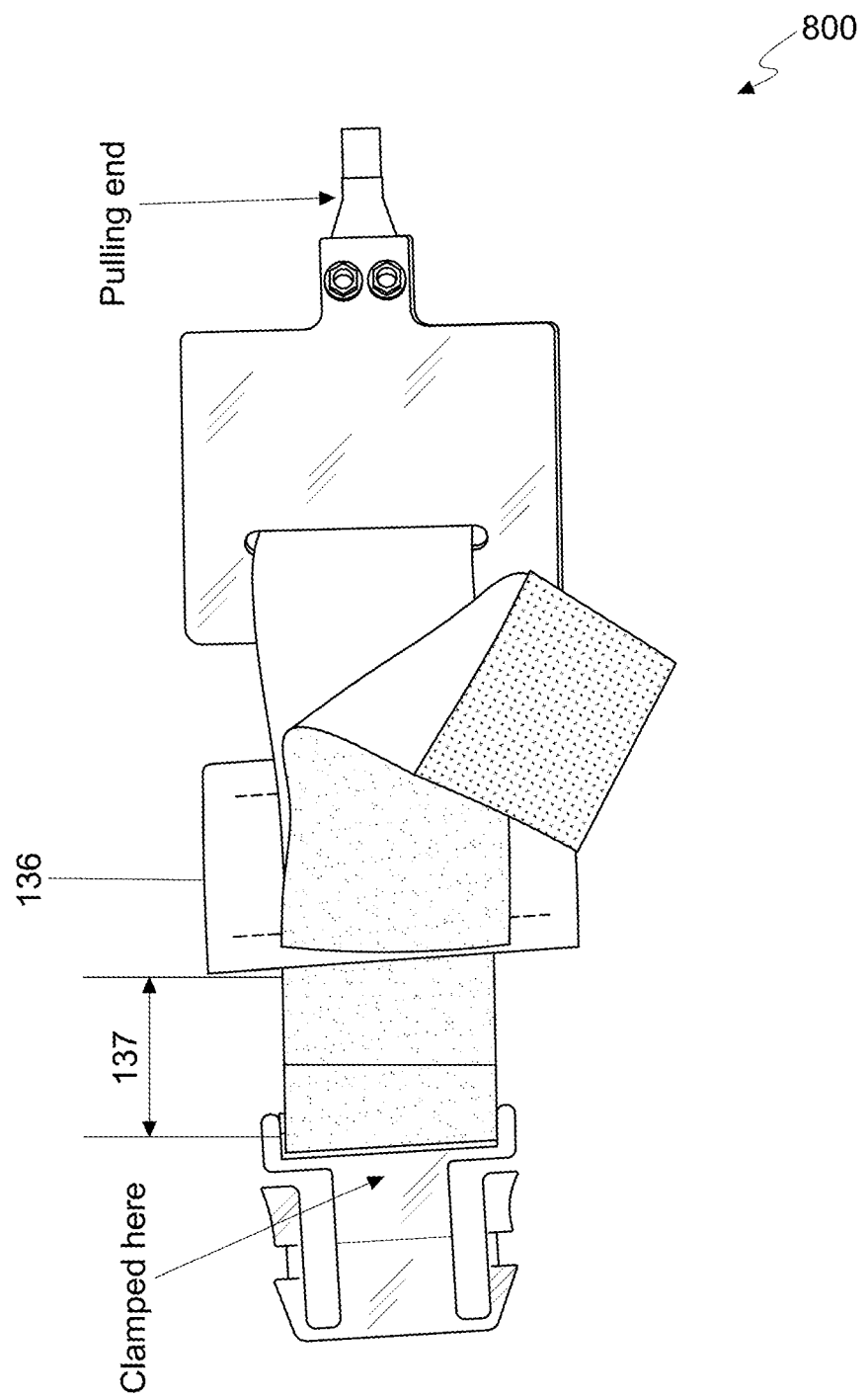
FIG. 8 is a photograph of a strap calibration arrangement for a tensile testing machine.
Figure 9:
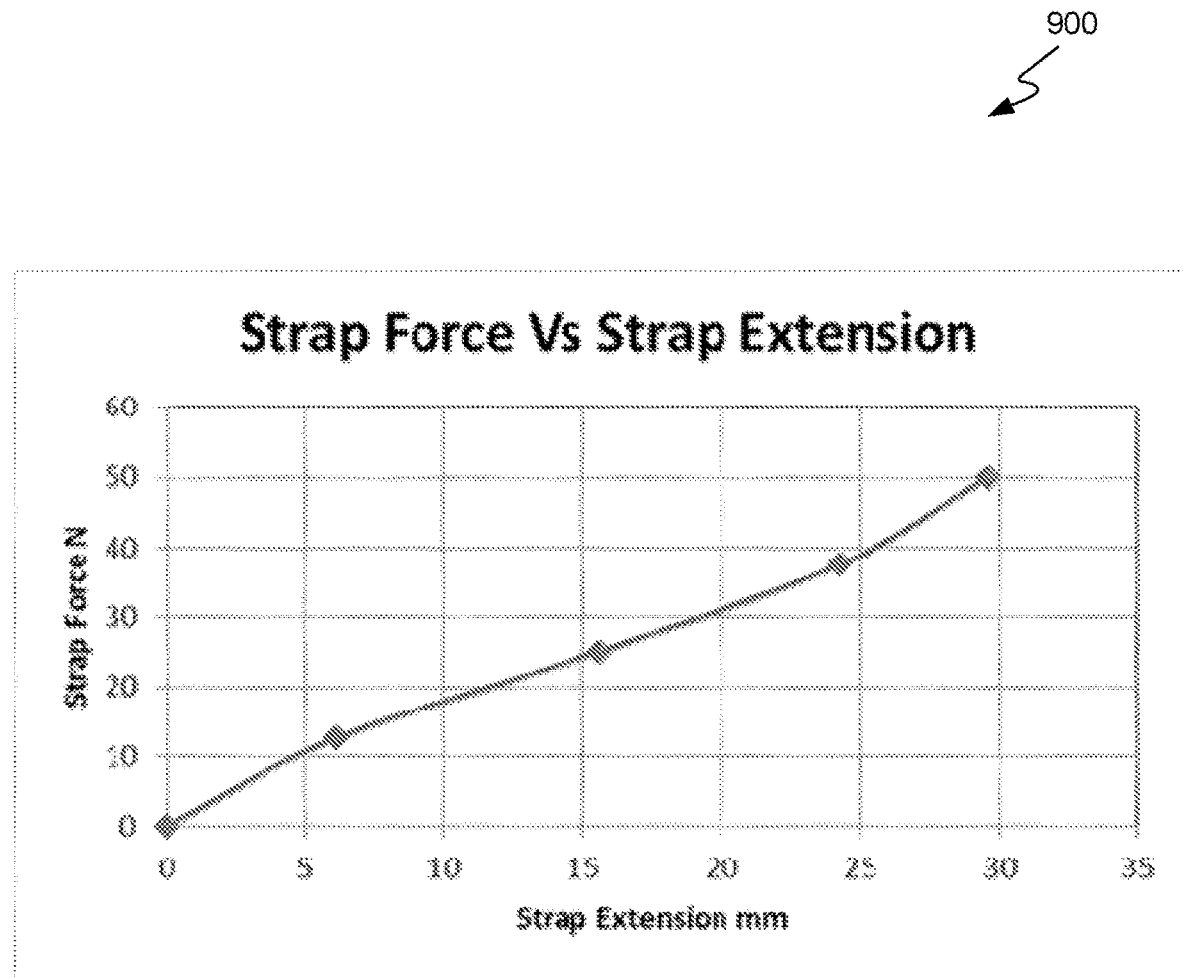
FIG. 9 is a graph of an exemplary relationship between compressive force and strapping extension of the compressive loading apparatus.

The extension length of the strapping 134 can then be calculated by subtracting the zero load calibration length from the length of the strapping 134 measured between the fastening mechanism and the strip. FIG. 8 shows a configuration 800 where the strapping 134 is extended by the calibration device 136. The calibration length 137 is related to the tensile force in the strapping 134 according to a calibration curve 900, as shown in FIG. 9. The calibration curve is determined via laboratory experimentation by pulling the strap under MRI-gantry conditions, and using a fixture reflecting the pulling and from load transfer point of view. A Tensile Testing Machine is used to perform the tests required for the calibration. The change in the calibration length 137 is also referred to as the "extension".

Discrete compressive load levels are thus associated with a particular strap extension length, allowing an operator of the loading component 130 to control the application of the compressive load to the individual's thorax, and to subsequently generate medical images of the compressed thorax.

2. Medical Imaging Equipment

In the medical imaging process, the scanner 106 generates diagnostic signals when an individual is placed in a predetermined position within the scanner 106, such as to enable the application of the diagnostic signals to the thoracic region. Selection of the diagnostic signal to perform the medical imaging process (including the configuration process in step 3 and the scanning process in step 4) depends upon the following factors:

i. the scanned image data requirements, such as whether or not the image details can be restricted to the bones or whether representations of other tissues are required (e.g. cartilages, muscles, internal organs and any other micro details for the simulation);

ii. the volume to be scanned and duration of scanning process; and iii. the tolerable exposure of the individual to the scanning environments (e.g. X-ray radiation, noise and fear).

MRI can be used as the diagnostic signal generated by the scanner 106, due to the relatively greater volume to be scanned, duration of the scanning process (in step 4) and details required. The skilled addressee will note that any one of the standard processes available for MRI, such as nuclear MRI (NMRI) or magnetic resonance tomography (MRT), may be used as an alternative.

3. Scanning Configuration

Figure 10:
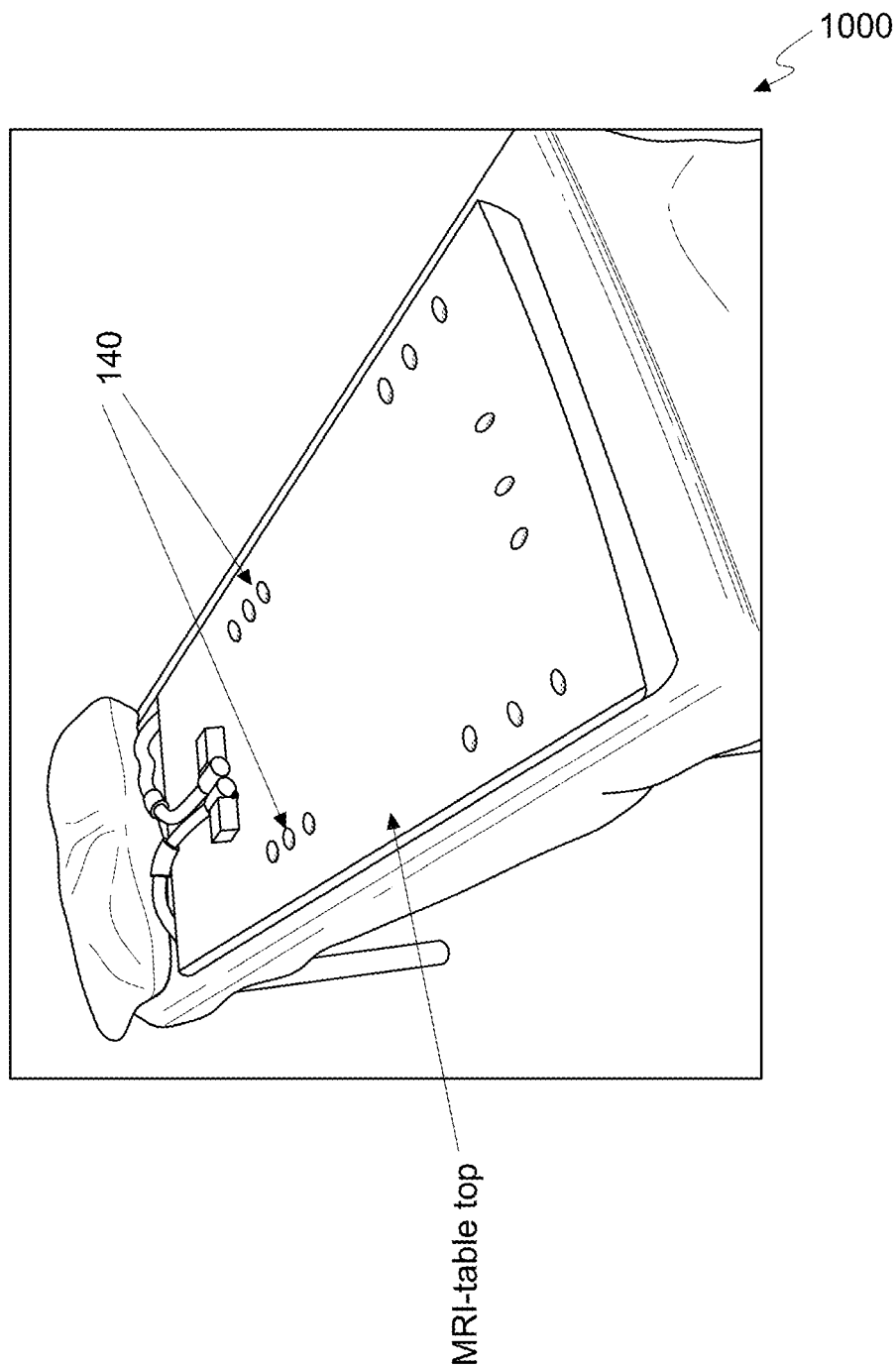
FIG. 10 is a photograph of a magnetic resonance imaging (MRI) table configured for simulation.

The MRI scanning configuration process 3 depends upon the size and the purpose of the simulation model to be build using scanned data. In the process 3, the scanner 106 is configured to generate diagnostic signals when an individual is placed in a predetermined position within the scanner 106, such as to enable the application of the diagnostic signals to the thoracic region. The individual is positioned inside the scanner 106, lying horizontally on a flat surface, such as a MRI table 1000 as shown in FIG. 10. Vitamin E capsules 140 are placed onto the surface to mark out the boundary of the surface in relation to the individual and compression plate 138, which is aligned parallel to the ground and to the scanning coils of the MRI scanner.

Figure 11:
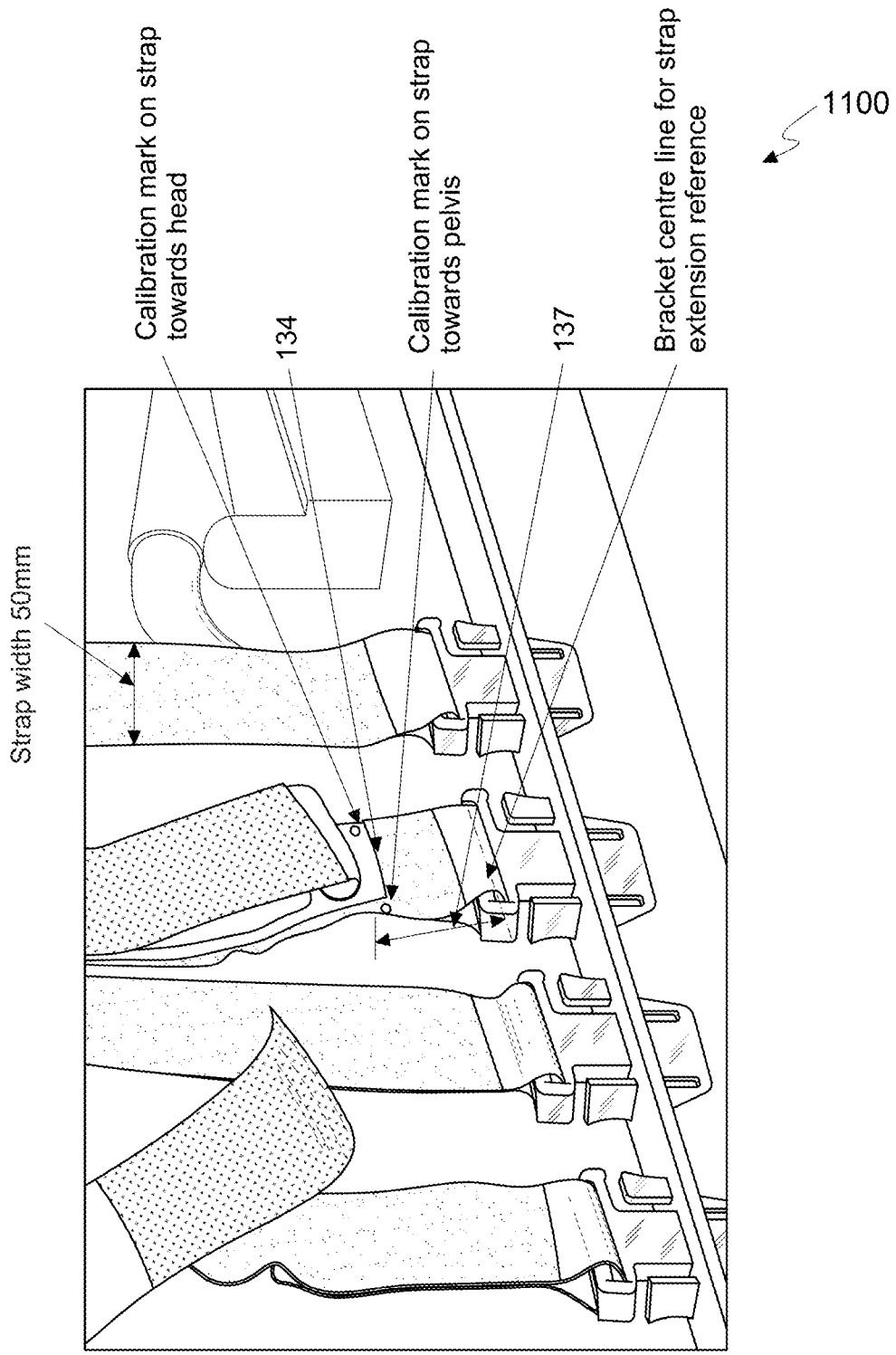
FIG. 11 is a photograph of a portion of the compressive loading apparatus during loading in a magnetic resonance imaging (MRI) gantry.

In the test scenario of reference, configuration is performed for scanning with the individual laid down on the MRI-couch and scanned from C4 to pubic symphysis without loading to obtain the data set. Individual then left the MRI-gantry. MRI-gantry is prepared for the next scanning under chest loading of the individual. Vitamin E-capsules 140 are pasted to the loading plate and the strap for determining the location of the loading plate and strap in the scanned data (FIGS. 6 and 7). The individual again laid down on the MRI-couch, the compression plate 138 is mounted on his chest as described in section 1.2 and the thoracic surgeon checked the accuracy of the positioning of the loading plate 138. FIG. 11 shows the details of the LHS end 1100 of the strap in this situation. The strap 134 is pulled gradually to give about 50 N force on each side of strap. Each time the changed calibration length 137 is measured using a plastic ruler. Individual is scanned under loaded condition from C4 to pubic symphysis. Data set is acquired from C4 to pubic symphysis for the load case maximum safe load.

Table 1(a) and 1(b) show the measured changed calibration length and load computations using strap stiffness calibration curve 900 (FIG. 9) from laboratory strap tests. Note, as the chest is not a smooth surface, the change of length of strap is not uniform across its width. Also the strap extension on LHS is different from that on RHS. Table 1(a) and 1(b) reflect this effect.

TABLE 1(a)

Strap extension and load reading for RHS strap.

| | RHS Strapping | | | | | |
|---|---|---|---|---|---|---|
| | Strap Edge Towards Head | | Strap Edge Towards Pelvis | | Av. | |
| Loading Level | Extended length (mm) | Extension Length (mm) | Extended length (mm) | Extension Length (mm) | Extension Length (mm) | Force (N) |
| No load | 38.1 | 0 | 0 | 0 | 0 | |
| Half Load | 55 | 16.9 | 55 | 16.9 | 16.9 | 25.2 |
| Full Load | 60 | 21.9 | 70 | 31.9 | 26.9 | 40.3 |

TABLE 1(b)

Strap extension and load reading for LHS strap.

| | LHS Strapping | | | | | |
|---|---|---|---|---|---|---|
| | Strap Edge Towards Head | | Strap Edge Towards Pelvis | | Av. | |
| Loading Level | Extended length (mm) | Extension Length (mm) | Extended length (mm) | Extension Length (mm) | Extension Length (mm) | Force (N) |
| No load | 38.1 | 0 | 0 | 0 | 0 | |
| Half Load | 55 | 16.9 | 55 | 16.9 | 16.9 | 25.2 |
| Full Load | 60 | 21.9 | 75 | 36.9 | 29.4 | 45.1 |

Although the described processes relate to MRI-based medical imaging, other methods may be utilised in order to produce medical imaging data based on the exposure of the individual to diagnostic signals by the imaging component 104. For example, computed tomography (CT), x-ray techniques or sonic based imaging (such as ultrasound) may be used in combination with the magnetic resonance based imaging techniques described herein. Additionally or alternatively, imaging component 104 can receive imaging data representing one or more images of the thorax region of the individual, allowing thorax modelling to proceed based, at least partially, on the received imaging data.

4. Scanned Data for No Load Case and Load Cases

The scanned data are produced according to the scanning process in step 4. If the volume to be scanned is too large to be scanned in one shot, the volume has to be scanned in more than one shot. The scan data obtained during different shots is merged to create one MRI data set for the individual undergoing scanning.

A Siemens Avanto 1.5 Tesla MRI scanner can be used to perform the scanning in the described embodiments. In an example configuration, the MRI scanner 106 has a maximum field of view of 500 mm length for one acquisition. As the volume to be scanned from C4 to pubic symphysis of the individual is larger than can be covered with a field of view 500 mm, overlapping shots are taken and shot data merged later on to one MRI data. The scanner 106 is configured to acquire two overlapping sets of images, each of 500 mm length, with an overlapping length of about 240 mm. Acquisition for each set of images takes about 30 seconds, during which the individual holds his breath. The MRI scanning process is completed over a period of approximately 10-15 minutes in total. Example, parameters used in the volume type acquisition process include: TR=5.45 ms; TE=2.39 ms; Flip angle=10 degrees; Slice thickness=2 mm; No. slices=144; Field of view=500 mm; Image Matrix=251× 256; and Acquisition time=30 s.

5. (Blank)

6. Scanned Data from External Sources

The system can receive pre-generated imaging data representing the medical images (e.g., in a pre-existing medical record) from an external source in step 6. The external scanned imaging data process in step 6 can be used additionally with, or as an alternative to, the scanning process in step 4.

7. Conversion of Scanned Data into Required Format for Down Stream Software

Following receipt of the imaging data, the logic module 116 commands (or "invokes") the conversion module 118, which processes the imaging data representing the received medical images in a conversion process. MRI staff operate the conversion module 118, via the UI 115, to convert the MRI raw data into various formats as required by the downstream software/users.

The conversion module 118 performs the format conversion process in step 6 on the merged image data to transform the merged data into a data format and type suitable for analysing, storing and transmitting medical images. The data format can be a medical format, e.g., the Digital Imaging and Communications in Medicine (DICOM) format. The formatted data object includes: data representing the merged medical image set; and attributes, including a dataset name and a quasi-unique dataset identifier (ID).

8. Segmentation of Scanned Data into Body Parts Using Third Party Software

The converted data contain all the components merged together representing their designations in the human body. The segmentation process in step 8 is performed to extract the sub-parts of the thorax anatomy from the data and store them individually. The segmentation process is performed by the conversion module 118, which interfaces with third-party software routines, such as, for example, those from the Mimics software package. The scanned data in DICOM format (see section 6) can be imported into the Mimics software directly by the operator using the UI 115. The conversion module 118 creates the data entries and performs the segmentation of the body parts as required for both the no load and maximum safe chest load cases. All sub-parts which play a role in the simulation model must be extracted from the scanned and converted data.

9. CAD-Parts from External Sources

The system can receive CAD-parts from external sources via an external sub-part importation routine in step 9.

10. Exporting Segmented Parts into a CAD-System to Produce CAD-Parts & Assemblies Alternatively, or in addition, the system can export the segmented sub-part representations to produce the CAD parts and assemblies in step 10. This process involves two sub-processes, as described hereinafter.

10.1 Exporting Segmented Parts into a CAD-System

The segmented body parts can be imported into a CAD-system using one of the commonly used data exchange formats as required, e.g. IGES, STL etc. The system is configured to export the individual body parts as one or more stereo lithography (STL) files through the conversion module 118. The STL files can be subsequently imported into a CAD-system e.g., the Catia™ system.

10.2 Produce CAD-Parts & Assemblies

Figure 12:
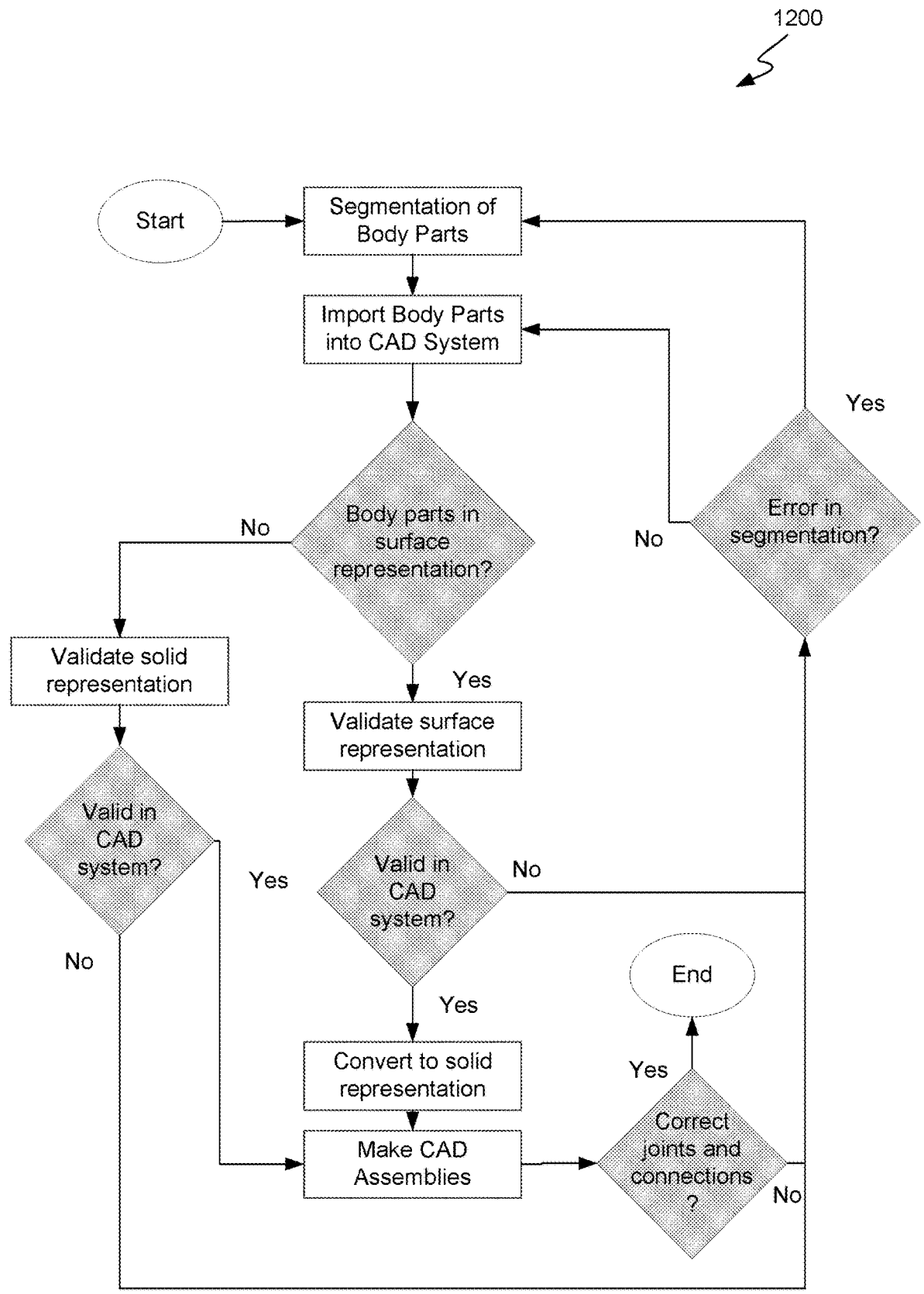
FIG. 12 is a flow diagram of a process for generating component data performed by the system and the apparatus.

The CAD-parts are produced from a well-defined geometric model of the thoracic sub-part. The segmented body parts imported into the CAD-system can be in the form of a surface representation or a solid representation. The system operates to generate the CAD-parts and assemblies with the correct geometry. This process can be important since any geometrical errors cannot be corrected through manipulation of the CAD-data in CAD-system. The system is configured to identify the source and nature of any errors, and to repeat the segmentation process to correct the errors if required. FIG. 12 shows the procedure or process 1200 for checking and correcting, wherever necessary, the CAD models (i.e., the CAD-parts and the CAD-assemblies), and thus generating the component data representing the thorax sub-parts in the form of the CAD models. The purpose of this process 1200 is to check and correct the geometry of the parts extracted from the MRI-data using third party software. These parts, after importing into the CAD System, are checked for conformity with CAD-model requirements, including surface, solid geometrical integrity requirements. Assemblies are checked for conformity with a person's body (in vivo). The segmentation data represent pixels, whereas the CAD data represent geometry, including solid geometry, points, lines, surfaces, solids definitions based upon mathematical definitions, and non-uniform rational basis spline (NURBS) curves and surfaces. Moreover, in the CAD data, the various body sub-parts should fit together as the corresponding body parts do in the in-vivo body representation. In contrast to mechanical engineering and manufacturing, if non-conformity issues are determined using the CAD checks, the sub-parts cannot be amended using the CAD tools to improve conformity with the CAD-system requirements, i.e., corrections cannot be made to the imported sub-parts in CAD System: instead, the process 1200 in FIG. 12 is used to locate the source of error and correct there.

No direct correction/manipulation of body parts is allowed in the CAD-System as it is in vivo and not a part drawn by hand by a draftsman or engineer.

The process 1200 includes the following steps:
 a) segmentation of the body parts;
 b) importing the body parts into the CAD system;
 c) determining whether the imported sub-parts are surface representations using a commercially available CAD tool;
 d) if the sub-parts are determined to be surface representations, then determining whether the surface representations are valid using a commercially available CAD validation tool;
 e) if the surface-representation sub-parts are determined to be invalid, determining whether there was an error in the segmentation;
 f) if it is determined that there was an error in the segmentation, returning to the segmentation step to correctly segment the body parts;
 g) if it is determined that there was no error in the segmentation, returning to the importation step to correctly import the body parts into the CAD system;
 h) if it is determined that the surface-representation sub-parts are valid, converting the surface representations to solid representations using commercially available CAD tools;
 i) once the solid representations are generated in the converting step, generating the CAD assemblies using the generated solid-representation sub-parts;

j) if it is determined that the sub-parts are not surface representations, assuming that the representations are solid representations and determining whether these solid representations are valid using a commercially available CAD validation tool;
k) if it is determined that the solid representations are valid, generating the CAD assemblies using the validated solid-representation sub-parts;
l) if it is determined that the solid representations are not valid, returning to the step of determining whether there was an error in the segmentation;
m) once the CAD assemblies are generated, determining whether the joints and connections represented in the assemblies are correct;
n) if it is determined that the joints and connections are not correct, returning to the step of determining whether there was an error in the segmentation; and
o) if it is determined that the joints and connections are correct, ending the process 1200.

Figure 13:
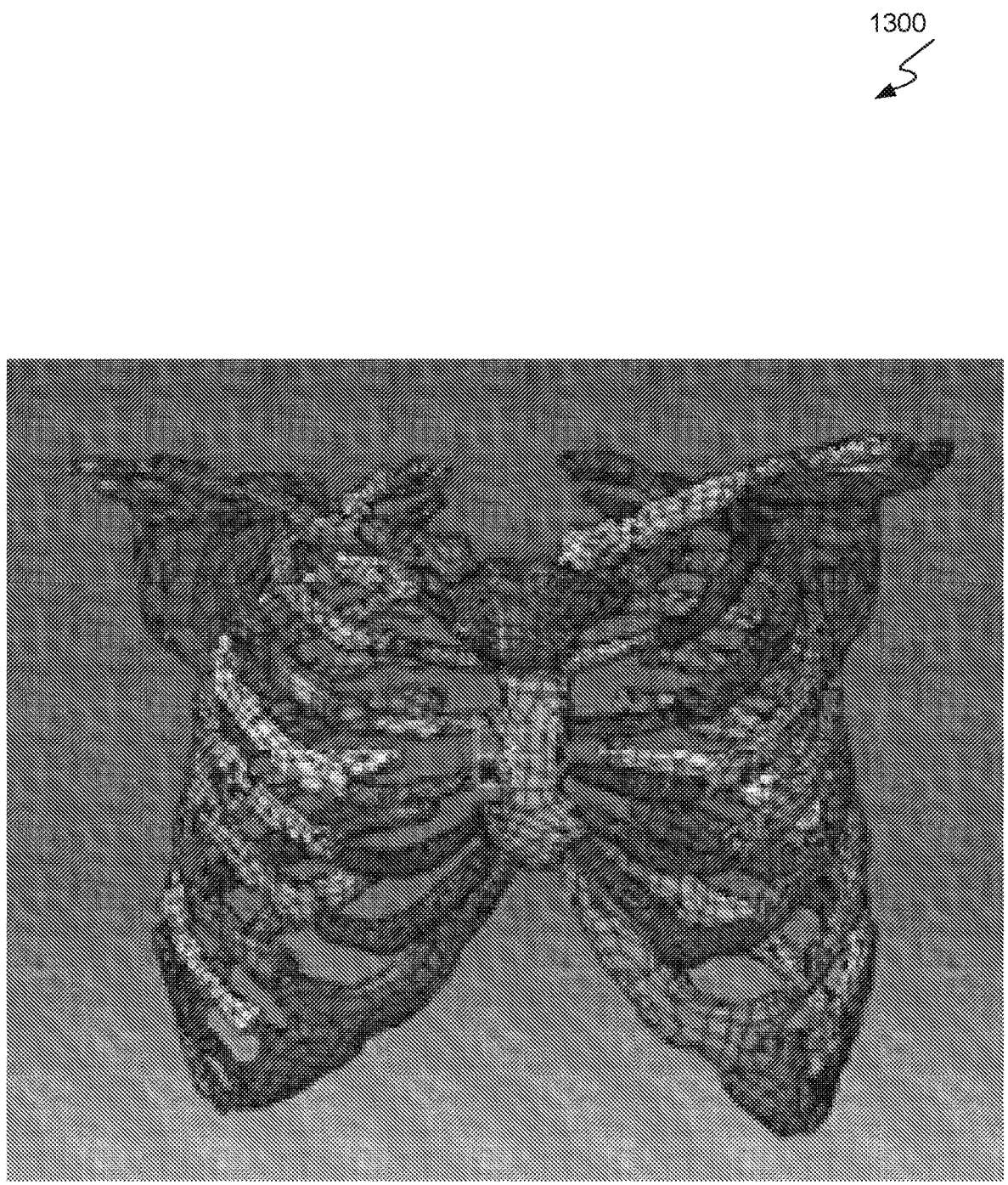
FIG. 13 is an illustration of a computer-aided design (CAD) model of the thorax.

In embodiments, body parts are imported in STL-format into the CAD-system CATIA. The parts imported are in the form of a surface representation in CATIA, and three-dimensional CAD-parts and CAD-assemblies are created based on these representations. An example of the total scanned volume CAD-assembly 1300, also called a CAD-model, is shown in FIG. 13. This CAD-model 1300 in CATIA of the scanned person (i.e. the individual in this specific case) contains: ribs, costal cartilages, humus, manubrium, sternum and scapula.

11. Exporting CAD-Parts into Finite Element Software

The CAD-parts constructed in step 10 can be exported into finite element software using an exchange data format, e.g. iges, one to one part transfer, etc. Exportation is performed via the simulation generation module 119, which is configured to access and use commercially available software modules, such as Abaqus/CAE™, to perform the finite element modelling. For example, the simulation generation module 119 can issue instructions to Abaqus modules to construct finite element representations based on a set of pre-configured default settings for each component to be included in the simulation. Alternatively or additionally, the simulation module 119 is configured to allow an operator to select sub-parts using the UI module 115.

12. Building Simulation Model Using Finite Element Software

The process of building the simulation model 12 is performed by the simulation module 119, and involves several sub-processes which are described hereinafter.

12.1 Creating the Finite Element Mesh

A finite element mesh is created (in step 121) from the sub-part component data (i.e. from the 3D CAD models representing the sub-parts of the thorax) using tools available in the finite element software. In the described embodiments of the system, the CAD-models are meshed using the tools available within the Abaqus software package.

12.2 Joint Simulation

The structural properties of the joints are simulated according to a joint simulation process 122. The simulation model 1400 produced reflects the anatomical and structural mechanics of the joint structure while accounting for the in-vivo mechanical properties of the materials used in the characterisation. Elements are selected in the finite element software to represent the joint properties and behaviour accordingly. The connections of these joining finite elements to the joining body parts reflect the in vivo behaviour of the joints.

Figure 14:
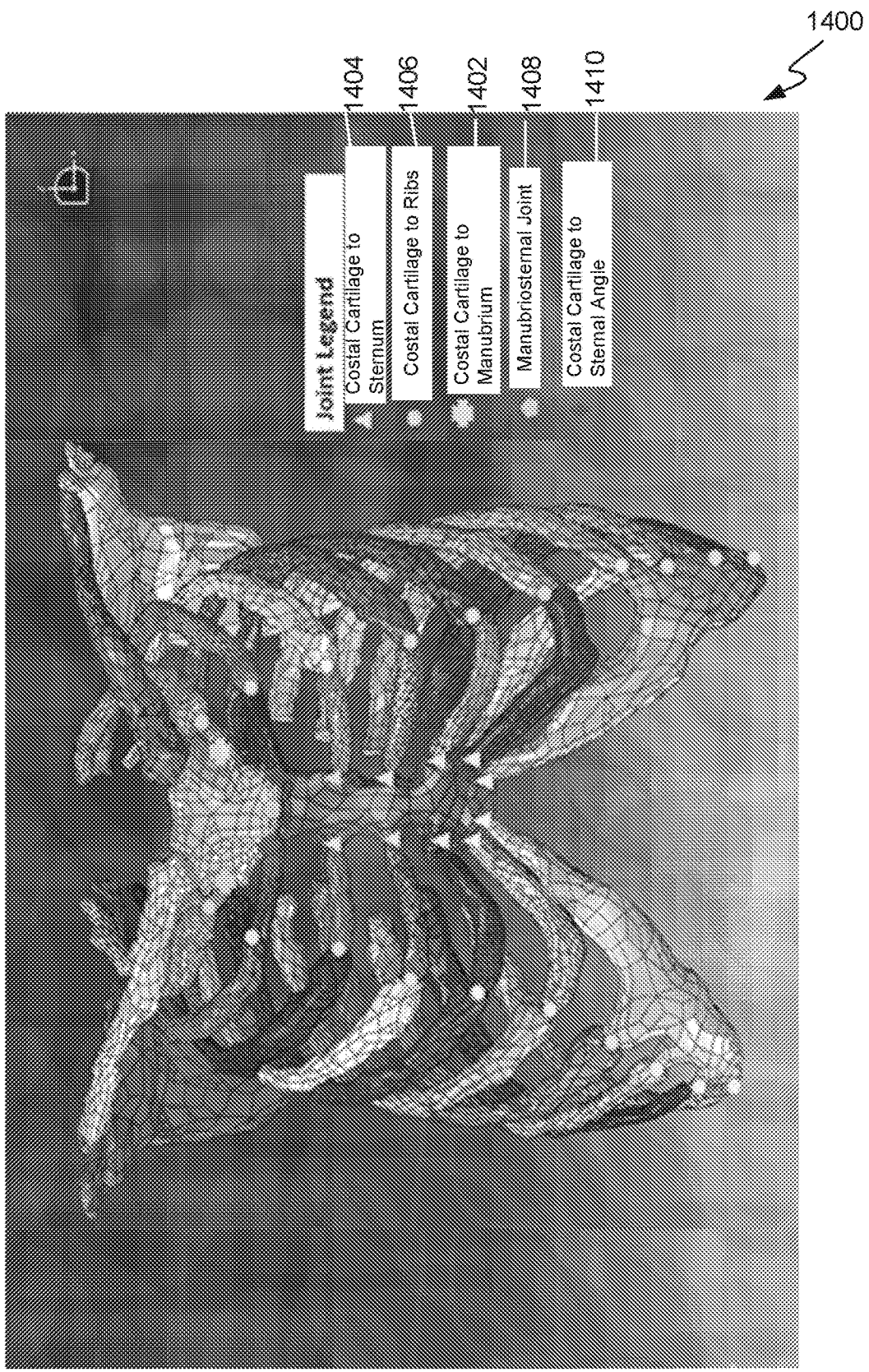
FIG. 14 is a front view of a thorax model indicating joints.

This joint simulation process 122 involves identification and modelling of the joints within the thorax including, the costal cartilage joints to the manubrium 1402, sternum 1404 and ribs 1406, sternal angle 1410, and the manubriosternal joint 1408, the scapula to clavicle joint, and the humerus and clavicle to manubrium joint, as shown in FIG. 14 for an example simulation model 1400.

The following joints modelled by the joint simulation process 122 in the described embodiments of the system include:
the second costal cartilage to sternal angle;
the manubriosternal joint;
the first costal cartilage to manubrium;
the third costal cartilage to sternum; and
the costal cartilage to rib.

12.2.1 Second Costal Cartilage to Sternal Angle

Figure 15:
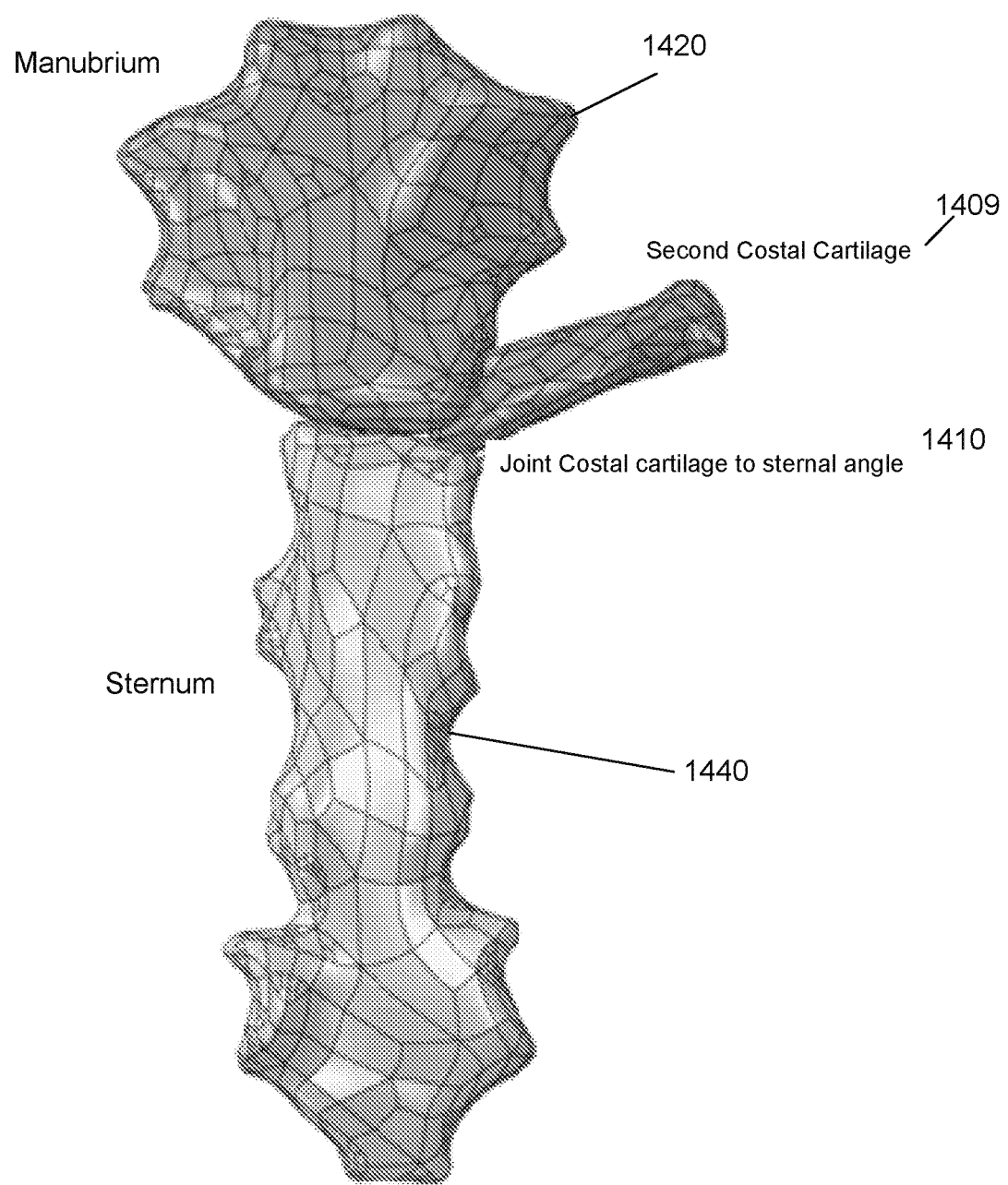
FIG. 15 is a perspective view of a second costal cartilage to sternal angle joint model.

This joint 1410 (second costal cartilage to sternal angle) connects the second costal cartilage 1409 to both the manubrium 1420 and the sternum 1440 and is strengthened anteriorly and posteriorly by fibres which radiate from the second costal cartilage 1409 on to the sternum 1440 and manubrium 1420. The cavity of this joint 1410 is divided into upper and lower parts through an intra-articular ligament as it covers both manubrium 1420 and sternum 1440 in that area. One dimensional dashpot elements with the axis following the line of action are used to simulate this joint 1410 keeping in mind the area covered by the radiate ligament (fibres), as shown in FIG. 15. For these dashpot elements, a spring stiffness of 100 N/mm and a dashpot coefficient of 10 N Sec/mm are used.

12.2.2 Manubriosternal Joint

Figure 16:
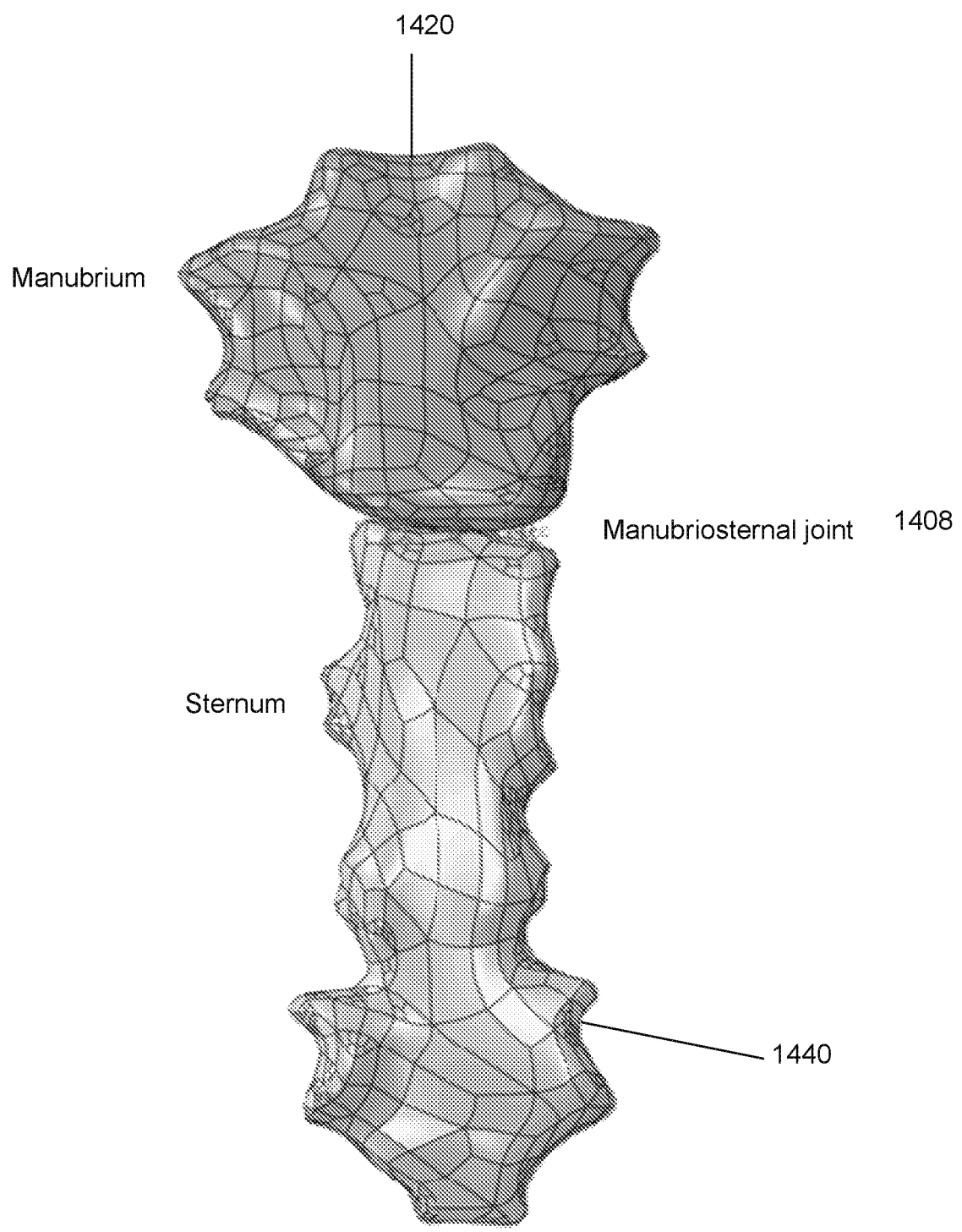
FIG. 16 is a perspective view of a manubriosternal joint model.

The manubriosternal joint 1408 lies between the manubrium 1420 and sternum 1440, as shown in FIG. 16. It is the early union, by hyaline cartilage, of the manubrium 1420 and the sternum 1440, which later becomes a symphysial type of joint 1410. One-dimensional dashpot elements with the axis following the line of action are used to simulate the joint 1408. For these dashpot elements a spring stiffness of 100 N/mm and a dashpot coefficient of 10 N Sec/mm are used.

12.2.3 First Costal Cartilage to Manubrium

Figure 17:
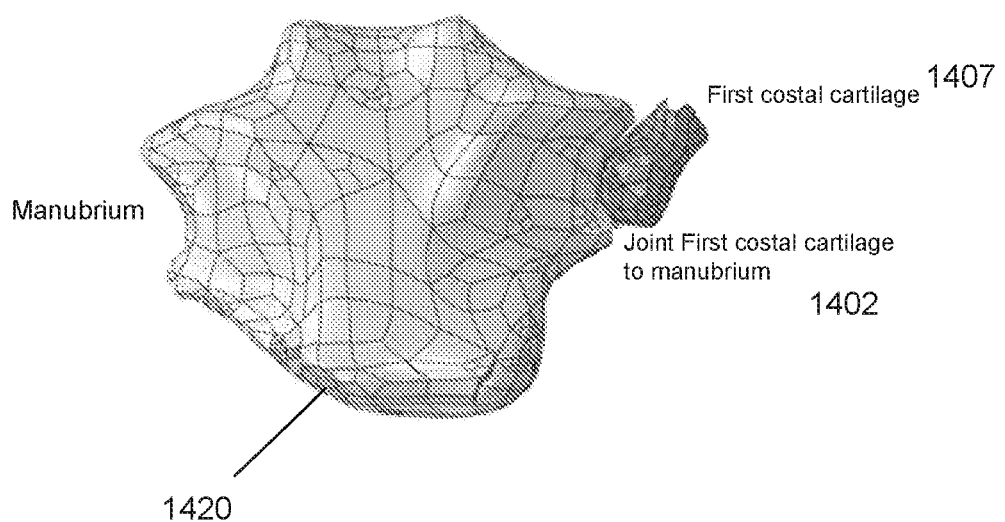
FIG. 17 is a perspective view of a first costal cartilage to manubrium joint model.

The first costal cartilage to manubrium joint 1402 is stiff, and does not allow relative movement between the first costal cartilage 1407 and manubrium 1420. One dimensional dashpot elements with the axis following the line of action are used to simulate the joint 1402 considering the area covered by the radiate ligament (fibres), as shown in FIG. 17. For these dashpot elements a spring stiffness of 100 N/mm and a dashpot coefficient of 10 N Sec/mm can be used.

12.2.4 Third Costal Cartilage to Sternum

Figure 18:
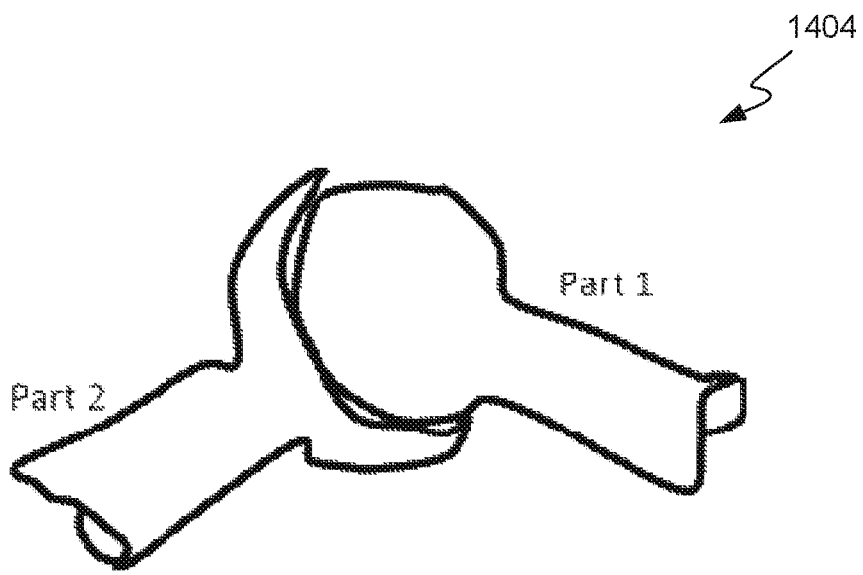
FIG. 18 is a schematic diagram of a spherical element model.
Figure 19:
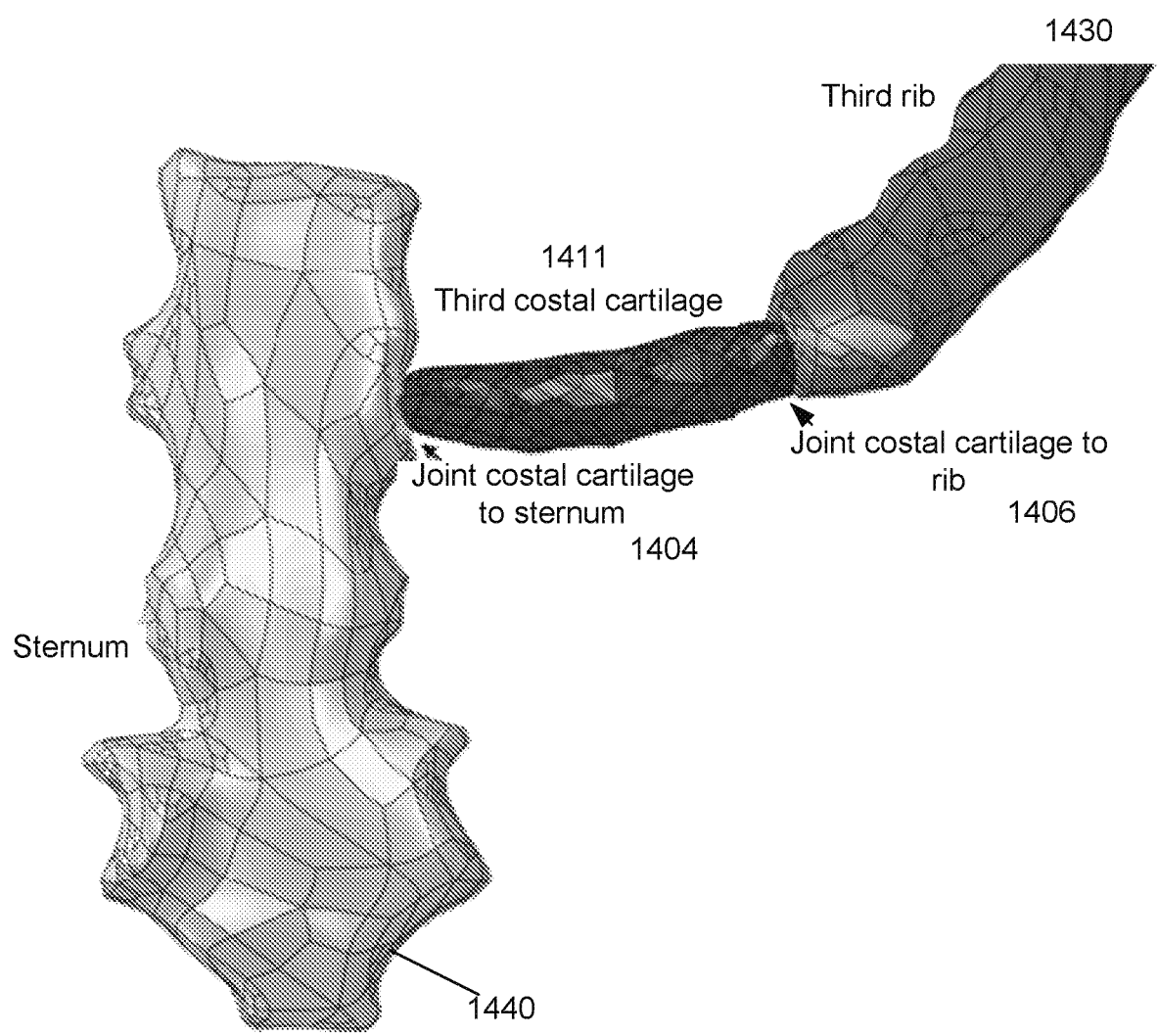
FIG. 19 is a perspective view of a third costal cartilage to sternum and third rib joint model.

This joint 1404 allows the relative rotation between the third costal cartilage 1411 and the sternum 1440. A spherical joint option (Abaqus), as shown in FIG. 18 in a structural mechanics sense, is used to simulate the joint, as shown in FIG. 19.

12.2.5 Costal Cartilage to Rib

Figure 20:
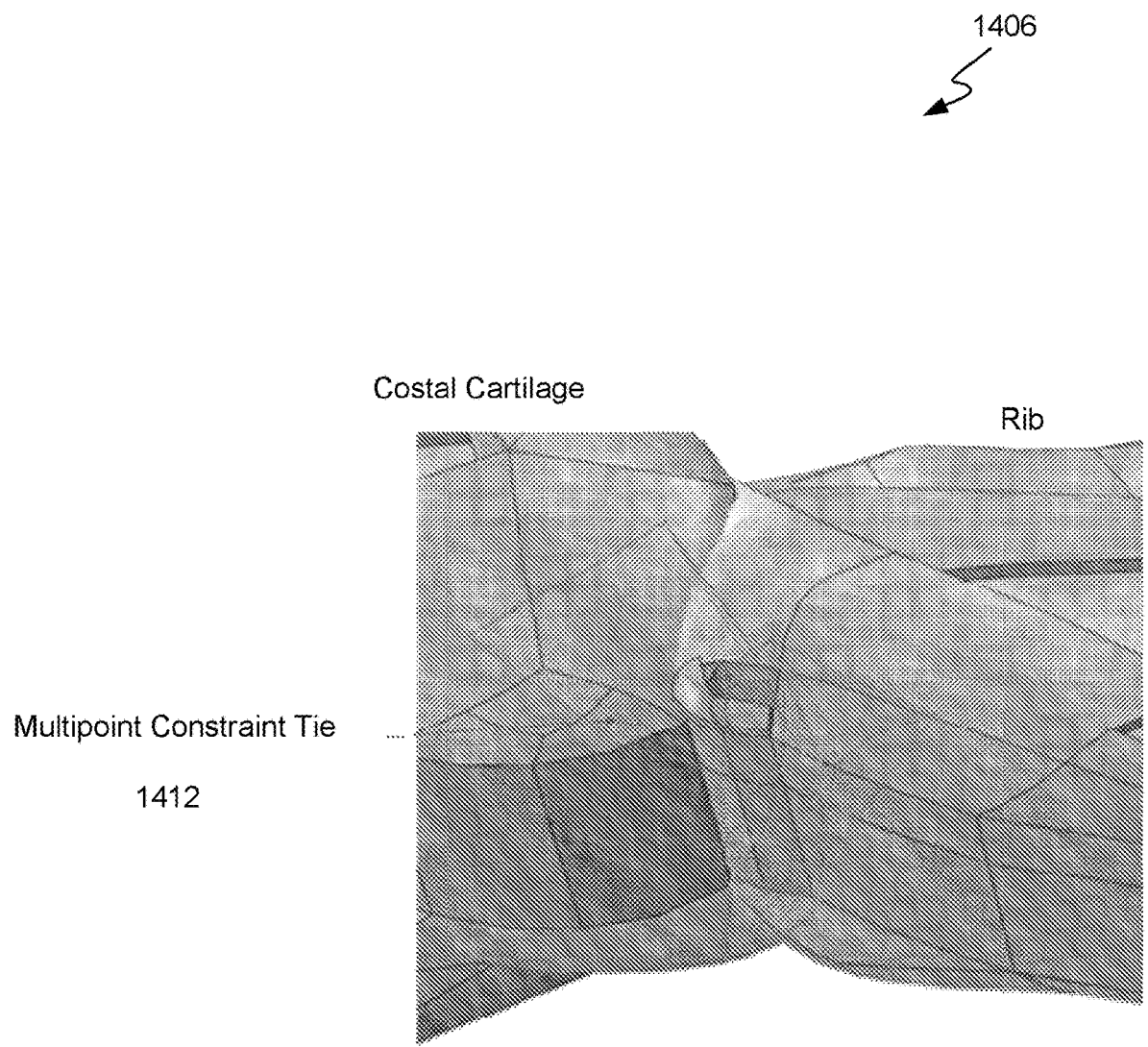
FIG. 20 is a perspective view of a multipoint constraint tie used in a costal cartilage to rib model.

All costal-cartilage-to-rib joints 1406, between a costal cartilage and a corresponding rib, are monolithic from a structural mechanics point of view. This means that the joining faces from costal cartilage and rib experience the same translator movement and there is no relative rotation between these two faces. A multipoint constraint (MPC) tie 1412 is used (in Abaqus) to simulate it, as shown in FIGS. 19 and 20.

12.3 Muscle Construction

Figure 21:
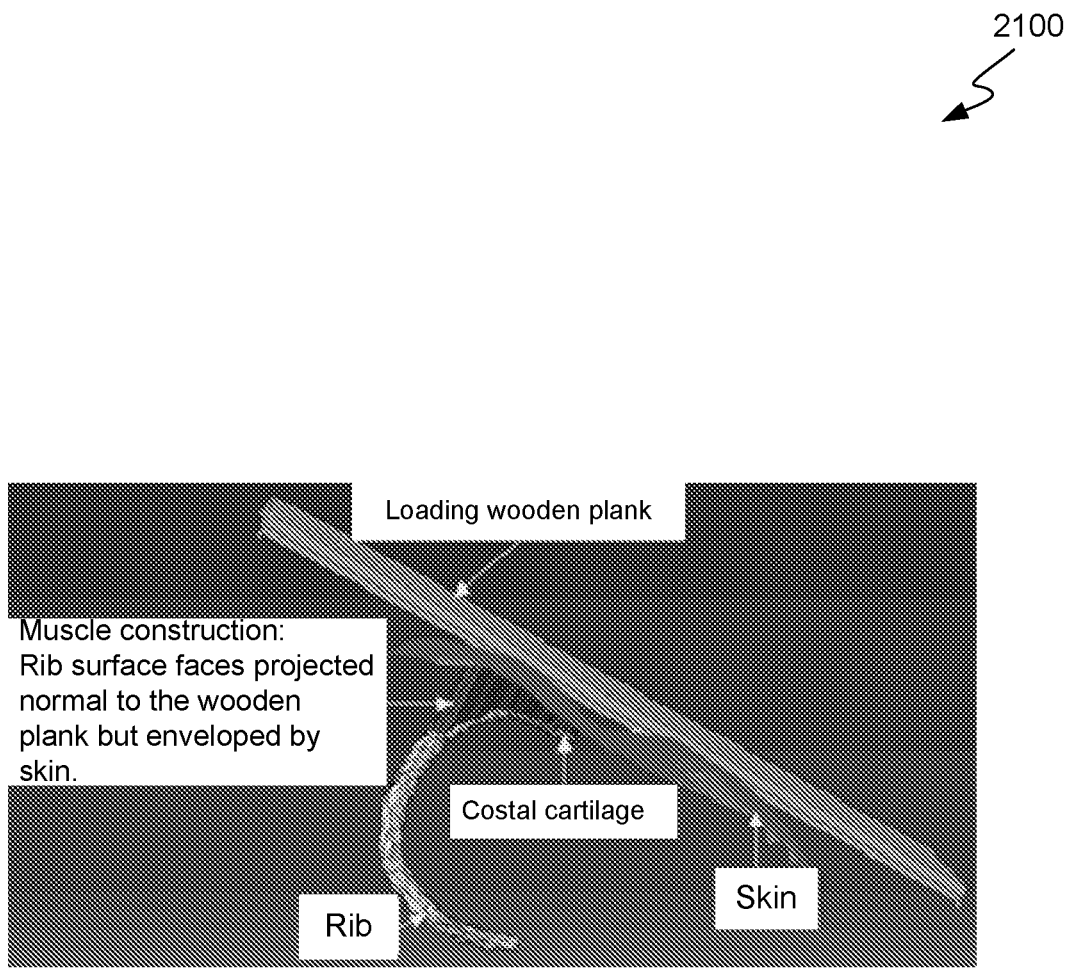
FIG. 21 is a side view of a thorax muscle model constructed by the system.

A muscle construction process in step 123 is performed by the simulation module 119. The main function of the muscles under the compression plate 138 is to distribute the vertical load over the individual's thorax. Models for the muscles 2100 are constructed in Abaqus. Alternatively, the system can be configured to segment the muscles in Mimics allowing for importation into Abaqus. The muscles are constructed by projecting rib surface normal to the plate 138 surface so that height is touching the surface enveloping the skin as shown in FIG. 21.

12.4 Boundary Conditions Simulation

Corresponding boundary conditions are applied to the simulation model 1400. Boundary conditions for the simulation model 1400 are determined by the simulation module 119 in the process 124. For example, the scapula of a person lying on an imaging table 1000 (or bed or bench) is simulated as being supported by dashpot elements that are grounded at one end and connected to the scapula surface at the other end. The vertebral column is not modelled explicitly. Each rib head is assumed to articulate with the vertebral body of its own number and that of the vertebra immediately above. Interarticular ligaments control the articulation and they are also connected to intervertebral fibrocartilage. These joints are simplified to grounded pin joints.

The straps 134 are not modelled in these conditions. To simulate their effect, the loading plate 138 is not allowed to move in lateral directions at the loading points but free to move in the vertical direction. Four grounded dashpot elements of stiffness 0.01 N/mm are attached to each upper corner of the loading plate 138 in the model to prevent initial numerical instability due to contact.

12.5 Load Simulation

Corresponding loads are applied to the simulation model 1400 in a loading simulation process 125. Section 4 illustrates the method of applying load to the individual. The vertical chest load is applied by pulling down the strap and tying the straps to hooks attached to the side of the MRI couch. The extension of the straps is measured on each side using a plastic ruler. From these extensions on each side and using the calibration curve 900 derived experimentally as explained in section 1.7.2, the vertical load applied to the plate 138 is determined on each side. The load values are as follows:

Right Hand Side Load=40 [N]; and
Left Hand Side Load=45 [N].

Figure 22:
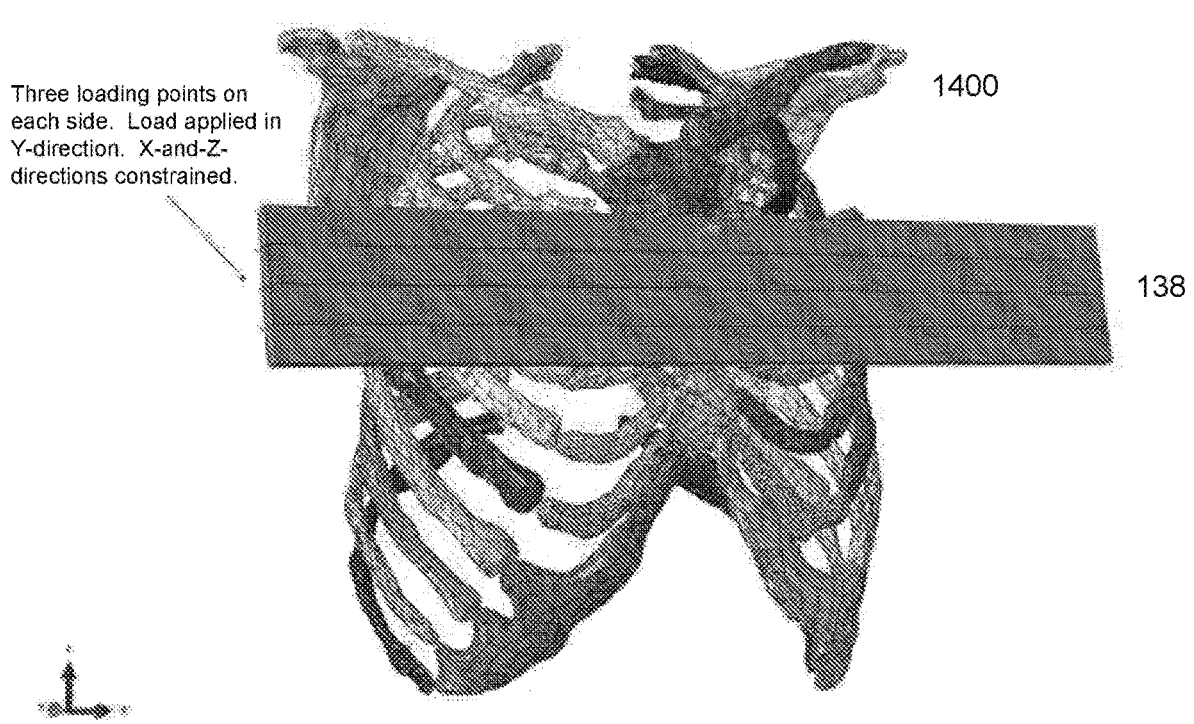
FIG. 22 is a perspective view of the compression plate model with the thorax model.
Figure 23:
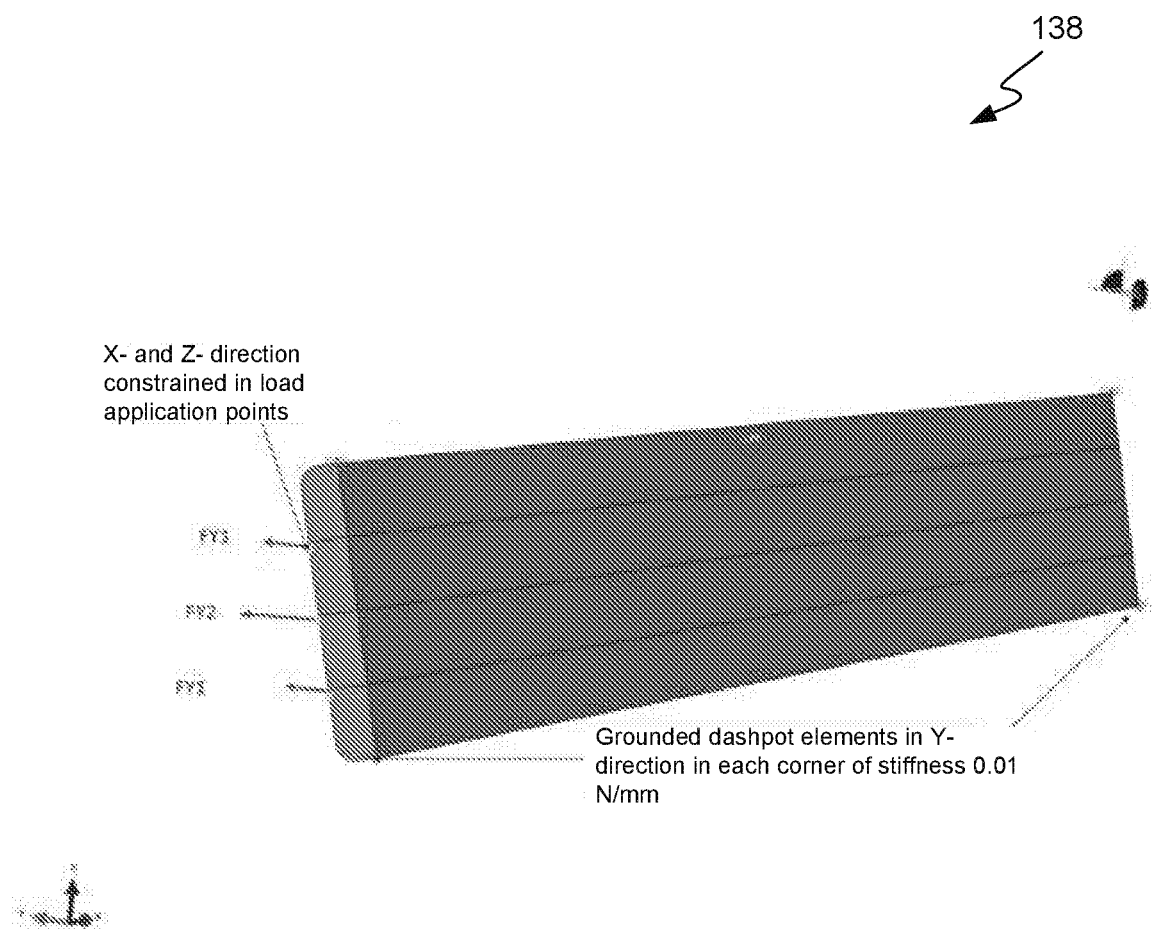
FIG. 23 is a perspective view of a model of the compression plate.

As load from straps acts through the slots 602 in the loading plate 138, the load is distributed and applied in three points on each side as point loads (FIG. 22). Point of application of forces FY1 and FY2 by the loading plate 138 are simulated as shown in FIG. 23. Table 2 shows the values of FY1 and FY2 for RHS and LHS.

TABLE 2

Point load values for RHS and LHS

|     | FY1 [N] | FY2 [N] |
| --- | --- | --- |
| RHS | 10 | 20 |
| LHS | 11.25 | 22.5 |

12.6 Material Properties

The corresponding material properties are assigned to the various parts in the simulation model 1400 by the material property application process 126. The properties used in the system shown in Table 3.

TABLE 3

Material properties

| No | Part | Material Properties |
| --- | --- | --- |
| 1 | Bones | Elastic, Young's Modulus = 2320 MPa & Poisson's ratio = 0.3 |
| 2 | Costal Cartilages | Elastic, Young's Modulus = 500 MPa & Poisson's ratio = 0.3 |
| 3 | Muscles | Hyperelastic, Isotropic, Mooney-Rivlin Material Model with three constants: C10 = 0.09; C01 = 0.023 and D1 = 0.0444; rubber of hardness Shore 20A. |
| 4 | Hard Wood for Compression Plate | Elastic, Young's Modulus = 15000 MPa & Poisson's ratio = 0.3 |

13. Processing Simulation Model

The simulation model 1400 produced by the model construction process in step 12 is processed using a solver from the Finite Element Software (such as Abaqus). The simulation module 119 is configured to interface with the software to input the simulation model 1400 data and invoke the solving routine.

14. Simulation Results

The simulation model processing results can be extracted, in the results extraction process in step 14, from the model solver used in step 13. The described system is configured to use the software Abaqus-CAE to perform the results extraction process from a ODB (Output Data Base) produced by Abaqus solver.

15. Results Obtained Externally

Alternatively, or in addition to, extracting the experimental results from a model solver (as described in section 14), the system can be configured to import external test and/or simulation results via the results importation process in step 15. The external results can be used to validate a generated simulation model, in accordance with the model validation process in step 16 described hereinafter.

For example, in the test scenario discussed herein, MRI-scan data obtained from the individual under maximum safe load is imported via the importation process for validation of the generated model. The scan data acquisition process under maximum safe load are explained in section 4. The MRI-data under maximum safe load is segmented using the Mimics software, so as to obtain the deformed shape of the body parts directly from in-vivo experimentation.

16. Correlation & Model Validation

Correlation testing and validation of the generated simulation model 1400 can be performed by the simulation module 119 in the model validation process, and using external results, as described in section 15.

For example, in the scenario discussed herein, deformed body parts are obtained by segmenting the MRI-data under full safe load (see section 15). The generated simulation model 1400 is based upon the MRI-data under no load. However, the position of the individual is changed in X-Z plane during data acquisition under maximum safe load as compared to that during data acquisition under no load, due to the individual leaving the MRI bed in preparation for the loading. He cannot occupy the same position within an accuracy of 2 mm (pixel size) after vacating the bed and lying again on his back for being loaded.

Figure 24:
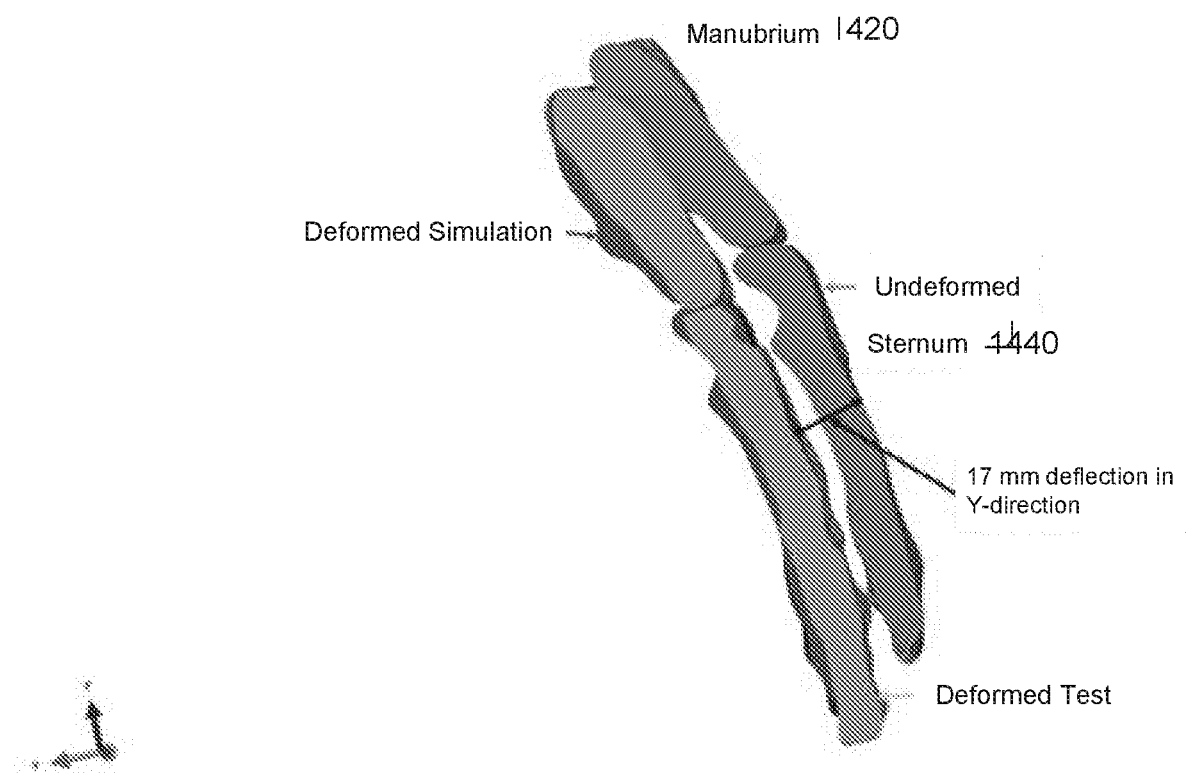
FIG. 24 is a side view of a manubrium & sternum assembly showing correlation and amount of deflection.

A "translatory" correction is performed for the deformed structure prior to superimposing it to the deformed structure obtained through simulation. To determine this correction, the simulation module 119 searches for a reference point which is not affected by the loading. The validation process 16 is configured to use a point on intervertebral disc between T1-T2 and closer to anterior cortex of vertebra, such that the sections through this point are compared. This may lead to 6 mm correction in X-direction and 12 mm correction in Z-direction. The correction is applied to the test-deformed parts. The body parts undeformed, test-deformed and simulation-deformed are superimposed and a correlation is established. FIG. 24 and Table 4 show the comparison in the scenario of the individual described herein. As can be seen from the comparison, there is a strong correlation between experimental results and results obtained through simulation, and the model is therefore validated in this case.

TABLE 4

Correlation summary.

|     |                                      | Y-displacement (mm) | |
| --- | ------------------------------------ | --- | --- |
| No  | Part Name                            | Simulation | Test |
| 1   | Manubrium                            | 19  | 18  |
| 2   | Sternum                              | 19  | 17  |
| 3   | Second Rib Left Hand Side            | 10  | 11  |
| 4   | Second Costal Cartilage Left Hand Side | 16 | 14 |
| 5   | Second Rib Right Hand Side           | 10  | 9   |
| 6   | Second Costal Cartilage Right Hand Side | 16 | 15 |
| 7   | Third Rib Left Hand Side             | 15  | 15  |
| 8   | Third Costal Cartilage Left Hand Side | 19 | 17  |
| 9   | Third Rib Right Hand Side            | 9   | 8   |
| 10  | Third Costal Cartilage Right Hand Side | 19 | 16 |

17. Usage of Simulation Model for the Development and Optimization of Person Specific Surgical Methods and Materials In the example scenario discussed herein, the produced simulation model 1400 is validated by the high level of correlation to the test results. The model 1400 can therefore be used in applications such as the development and optimization of person specific surgical methods and materials. Selection and adaption of surgical methods and surgical tools may be performed based on the unique anatomical characteristics of the individual in order to improve surgical procedure efficiency and safety. Furthermore, the person-specific thorax modelling apparatus, system and process may provide an improved simulation of the bone structures and soft tissue regions of the particular individual.

What is claimed is:

1. A process for in-vivo person-specific thorax simulation modelling, including:
receiving imaging data representing one or more images of a thorax of an individual, wherein the received imaging data are generated by:
determining one or more compressive load levels to be applied to the thorax of the individual, wherein the one or more compressive load levels are determined based on a maximum safe load level which can be applied to the individual's thorax;
applying one or more of the determined compressive loads to the thorax of the individual;
generating, for each of said applied compressive load levels, the imaging data representing the one or more images of the thorax region of the individual, when the said compressive load level is applied to the thorax of the individual;
processing the imaging data to generate component data representing one or more thorax sub-parts of the individual, including one or more joints adjacent to a costal cartilage or a sternum of the individual, by:
merging a plurality of images represented by the imaging data;
converting at least a subset of the merged imaging data into a standard medical image data format;
segmenting at least a subset of the converted data to isolate individual anatomical sub-parts of the thorax;
producing a three-dimensional representation for each of the segmented sub-parts of the thorax; and
representing the structural properties of the thorax of the individual, including the properties of the one or more joints, by:
constructing a finite element mesh from the component data of one or more of the sub-parts of the thorax; and
representing the structural properties of the one or more joints using:
a dashpot element for:
the manubriosternal joint;
the first costal cartilage to manubrium joint; and
the second costal cartilage to sternal angle;
a spherical element for the third costal cartilage to sternum joint; and
a multipoint constraint element for each costal cartilage to rib joint.

2. The process of claim 1, wherein the one or more images represented by the imaging data are images of bones and soft tissue of the thorax of the individual.

3. The process of claim 1, wherein the imaging data are converted to the Digital Imaging and Communications in Medicine (DICOM) format.

4. The process of claim 1, wherein the three-dimensional representation of each thorax sub-part is a Computer Aided Design (CAD) model.

5. The process of claim 1, further comprising generating the imaging data.

6. The process of claim 5, wherein the imaging data are generated by subjecting at least the thorax region of the individual to Magnetic Resonance Imaging (MRI).

7. The process of claim 1, wherein the one or more compressive load levels are applied to the thorax by a compressive loading apparatus, said apparatus configured to exert a compressive force onto the thorax of the individual in a direction transverse to the plane of the surface of the thorax.

8. A system configured to perform the process of claim 1.

* * * * *